United States Patent [19]

Butterfield et al.

[11] Patent Number: 5,261,412
[45] Date of Patent: Nov. 16, 1993

[54] METHOD OF CONTINUOUSLY MONITORING BLOOD PRESSURE

[75] Inventors: Robert D. Butterfield, Poway; Stephen A. Martin, Carlsbad, both of Calif.

[73] Assignee: IVAC Corporation, San Diego, Calif.

[21] Appl. No.: 980,931

[22] Filed: Nov. 20, 1992

[51] Int. Cl.⁵ .............................................. A61B 5/02
[52] U.S. Cl. ..................................... 128/672; 128/687
[58] Field of Search ............... 128/672, 676, 677–683, 128/687–688, 690–691

[56] References Cited

U.S. PATENT DOCUMENTS

| | | | |
|---|---|---|---|
| 4,269,193 | 5/1981 | Eckerle | 128/672 |
| 4,423,738 | 1/1984 | Newgard | 128/672 |
| 4,718,428 | 1/1988 | Russell | 128/677 X |
| 4,802,488 | 2/1989 | Eckerle | 128/672 |
| 4,836,213 | 6/1989 | Wenzel et al. | 128/672 |
| 4,860,760 | 8/1989 | Miyawaki et al. | 128/680 |
| 4,893,631 | 1/1990 | Wenzel et al. | 128/672 |
| 4,928,701 | 5/1990 | Harada et al. | 128/677 |
| 4,951,679 | 8/1990 | Harada | 128/672 |
| 4,987,900 | 1/1991 | Eckerle et al. | 128/672 |
| 5,119,822 | 6/1992 | Niwa | 128/672 |
| 5,154,680 | 10/1992 | Drzewiecki et al. | 128/672 |
| 5,158,091 | 10/1992 | Butterfield et al. | 128/672 |

Primary Examiner—Kyle L. Howell
Assistant Examiner—Angela D. Sykes
Attorney, Agent, or Firm—Dykema Gossett

[57] ABSTRACT

A method, for use in a non-invasive blood pressure monitoring system, of operating a tissue stress sensor at an off-optimum arterial applanation state. The system uses a stress sensor including a stress sensitive element for detecting stress of tissue overlying an artery of interest. The tissue stress sensor is placed in communication with tissue overlying the artery of interest and at least one electrical signal is obtained therefrom representing stress data across the length of the stress sensitive element. The data represents stress datum communicated to preselected portions of the stress sensitive element. From the stress datum, various techniques are used to determine the optimum applanation state and the actual applanation state. A waveform scaling factor function is created which compensates for the errors associated with operating the tissue stress sensor at an off-optimum applanation state. Thus, the disclosed method provides the benefits associated with operating a tissue stress sensor at an off-optimum state without sacrificing measurement accuracy.

25 Claims, 16 Drawing Sheets

METHOD OF CONTINUOUSLY MONITORING BLOOD PRESSURE

TECHNICAL FIELD

The present invention generally relates to pressure measurement systems, and more particularly relates to a method for non-invasively, and continuously determining the intra-arterial blood pressure of a wearer.

BACKGROUND OF THE INVENTION

Systems for measuring the intra-arterial blood pressure of a patient can be subdivided into two main groups—those which invade the arterial wall to access blood pressure and those which use non-invasive techniques. Traditionally, the most accurate blood pressure measurements were achievable only by using invasive methods. One common invasive method involves inserting a fluid filled catheter into the patient's artery.

While invasive methods provide accurate blood pressure measurements, the associated risk of infection and potential for complications, in many cases, outweigh the advantages in using invasive methods. Because of these risks associated with invasive methods, a non-invasive method, known as the Korotkoff method is widely used.

The Korotkoff method is known as an auscultatory method because it uses the characteristic sound made as the blood flows through the artery to mark the points of highest (systolic) and lowest (diastolic) blood pressure. Although the Korotkoff method is non-invasive, it only provides a measurement of selected pressure points (i.e., the highest pressure point and the lowest pressure point) along the continuous pressure wave. While, in many instances, systolic and diastolic pressure are sufficient for accurate diagnosis, there are many applications in which it is desirable, or required, to monitor and utilize the entire continuous curve of the blood pressure wave. In these applications, the Korotkoff method is simply incapable of meeting this requirement. In addition to this limitation of the Korotkoff method, it also has an additional limitation of necessitating the temporary occlusion (complete closing) of the artery in which blood pressure is being monitored. While arterial occlusion is not prohibitive in many applications, there are occasions where the patient's blood pressure must be monitored continuously (such as when undergoing surgery) and accordingly, the prohibiting of blood flow, even on a temporary basis, is undesirable.

Because of the above-mentioned risks involved with invasive blood pressure measurement, and the shortcomings of the Korotkoff method, extensive investigation has been conducted in the area of continuous, non-invasive blood pressure monitoring and recording. Some of these non-invasive techniques make use of tonometric principles which take advantage of the fact that as blood pressure flows through the arterial vessel, forces are transmitted through the artery wall and through the surrounding arterial tissue and are accessible for monitoring at the surface of the tissue. These forces, under certain conditions, can be used to determine intra-arterial blood pressure.

Because the tonometric method of measuring blood pressure is non-invasive, it is used without the risks associated with invasive techniques. Furthermore, in addition to being more accurate than the Korotkoff method discussed above, it has the capability of reproducing the continuous blood pressure waveform, as opposed to the limited systolic and diastolic pressure points provided by the Korotkoff method.

Because the accuracy of tonometric measurements depend heavily upon the method and apparatus used to sense tissue forces, several sensors have been specifically developed for this purpose. For example, U.S. Pat. No. 4,423,738 issued to Newgard on Jan. 3, 1984 discloses an electromechanical force sensor which is made up of an array of individual force sensing elements, each of which has at least one dimensions smaller than the lumen of the underlying artery wherein blood pressure is to be measured. Also, U.S. Pat. No. 4,802,488 issued to Eckerle on Feb. 7, 1989, discloses an electromechanical transducer that includes an array of transducer elements. The transducer elements extend across an artery with transducer elements at the ends of the array extending beyond opposite edges of the artery. Additionally, U.S. patent application Ser. No. 07/500,063 and U.S. patent application Ser. No. 07/621,165 both disclose tonometric sensors for use in determining intra-arterial blood pressure. Each of the above four mentioned patents/patent applications disclose transducers having sensing portions that span well beyond the lumen (opening) of the underlying artery. One main reason it is advantageous to construct a sensor in this manner is because the arteries of interest are relatively small and difficult to locate. By constructing tonometric sensors which employ a relatively long sensing area, the placement of the sensor by a technician, is not as critical as it would be if the sensor was capable of only sensing along a narrow region.

Although by constructing a tonometric sensor with a long sensing portion, the technician's task is simplified, it introduces certain complexities into the methodology used for determining intra-arterial blood pressure. For example, because the sensor face is made relatively long as compared to the lumen of the underlying artery, only a small fraction of the sensing portion of the tissue stress sensor is overlying the artery, and it is only this portion which is sensing useful forces (i.e. forces which are related to intra-arterial blood pressure). The remaining portion of the sensing portion is in contact with tissue which does not overlie the artery of interest, and accordingly, does not transmit forces to the sensing portion which can be used for determining intra-arterial pressure.

Therefore, in view of the above complexities, when employing tonometric sensors of the type discussed above, before the accurate intra-arterial blood pressure can be determined, a method must be employed for determining which portion of the sensor is best positioned over the artery of interest for determining the intra-arterial blood pressure. One such method is disclosed in U.S. Pat. No. 4,269,193 issued to Eckerle on May 26, 1981. The method disclosed in the '193 patent includes selecting the transducer element which has a maximum pulse amplitude output and then looking to its neighbors and choosing the neighbor having a spatially local minimum of at least one of the diastolic and systolic pressures. Other methods are disclosed in U.S. Pat. No. 4,802,488 issued to Eckerle on Feb. 7, 1989. In the '488 patent the following methods are disclosed, a curve-fit method, a two-humps method, a center-of-gravity method, and a "catch-all" method which includes using one of the three aforementioned methods in conjunction with externally supplied user information (such as sex, height, age, etc.). Also, U.S. Pat. No.

4,893,631 issued to Wenzel, et al. on Jan. 16, 1990, discloses a method for determining which sensor in an array of sensors best tracks the pulse in an underlying artery using a spatially weighted averaging method. This method employs the steps of finding local diastolic pressure minimums, selecting the number of transducers spanning the local minimums, computing the spatially weighted average from elements centered about the local minimums and computing a weighted average therefrom.

In addition to the sensor's function to measure tissue stress, the sensor also functions to applanate (or flatten) the artery of interest. Applanating the artery of interest is critical in correctly determining intra-arterial blood pressure. In fact, it has been found, that when the artery of interest is applanated to an optimum state, accurate determinations of intra-arterial blood pressure can be made. U.S. Pat. No. 4,799,491 issued to Eckerle on Jan. 24, 1989 discloses a method for determining a "correct" hold down pressure. Additionally, U.S. Pat. No. 4,836,213 issued to Wenzel on Jun. 6, 1989 discloses a method for computing optimum hold down pressure for a transducer indicative of blood pressure in an artery.

Although the above-referenced methods may yield some degree of success, they are not without their drawbacks. Specifically, when placing a tonometric sensor against the tissue of a patient, it has generally been accepted that in order to obtain accurate data, the sensor must be pressed against the tissue to the extent that it causes the underlying artery to applanate to an optimum degree or state. However, patient comfort is sacrificed if the tonometric sensor remains in this position for a long period of time due to the tissue displaced by the tonometric sensor in order to maintain optimum artery applanation. Thus, it is believed that there is need for a method of using the tonometric sensor which does not necessitate maintaining an optimum arterial applanation state for long periods of time while still providing a continuous, accurate indication of intra-arterial blood pressure.

Thus, it is an object of this invention to provide a method or methods of operating a tonometric sensor at a non-optimum applanation state while still providing an accurate, continuous indication of intra-arterial blood pressure.

The methodologies set forth herein for achieving this object generally include a technique for determining an error factor, or factors, associated with operating the tonometric sensor at a non-optimum, or off-optimum, applanation state. Accordingly, when tissue stress data is collected by the tonometric sensor in its off-optimum applanation state, the error correction factors are used to operate on the stress data in a way which produces a corrected signal which accurately reflects the intra-arterial blood pressure.

SUMMARY OF THE INVENTION

In light of the foregoing objects, the present invention provides for use in a non-invasive blood pressure monitoring system, a method of operating a tissue stress sensor at a non-optimum arterial applanation state. The tissue stress sensor includes a stress sensitive element for measuring the stress of tissue overlying an artery of interest. The stress sensitive element is sufficiently long such that it exceeds the lumen of the artery of interest. The method includes the steps of: (A) placing the stress sensitive element of the tissue stress sensor in communication with the tissue overlying the artery of interest, (B) orienting the stress sensitive element such that it spans beyond the lumen of the artery of interest, (C) using the stress sensitive element to act upon the artery of interest thereby applanating the artery of interest through a plurality of applanation states, and at each applanation state, (D) obtaining from the tissue stress sensor at least one electrical signal representing stress data across the length of the stress sensitive element, each stress datum of said stress data representing stress datum communicated to a predetermined portion of the stress sensitive element from the tissue overlying the artery of interest, and from the data obtained in at least one of the plurality of applanation states, (E) determining an optimum arterial applanation state, (F) computing an error value associated with the non-optimum arterial applanation state wherein the non-optimum arterial applanation state is different from the optimum arterial applanation state, (G) applanating the artery of interest to the non-optimum arterial applanation state, and while the artery is applanated to the non-optimum applanation state, (H) obtaining tissue stress data from the tissue stress sensor, and (I) combining the stress data obtained in step (H) with the error value computed in step (F) to yield corrected stress data that approximates intra-arterial blood pressure.

DETAILED DESCRIPTION OF THE PREFERRED EMBODIMENTS

Figure 1:
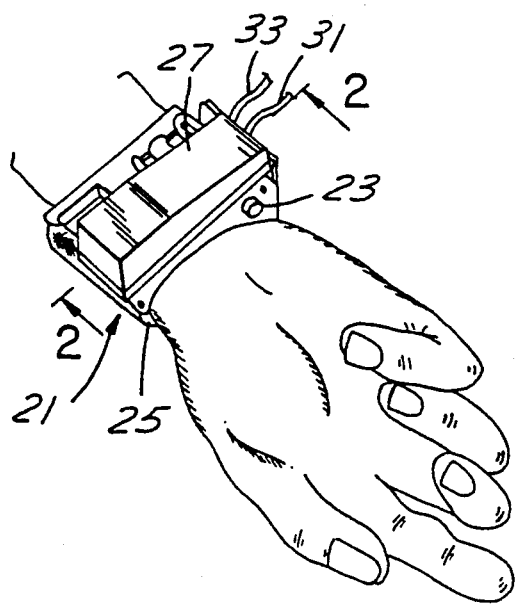
FIG. 1 is a perspective view of a tissue stress sensor attached to the wrist of a wearer.

Now referring to FIG. 1, wrist mount apparatus 21 includes base 23 and flexible strap 25. Flexible strap 25 is adapted to engage base 23 to the wrist of a user. Tissue stress sensor housing 27 is fastened to base 23 and houses a tissue stress sensitive element 34 (tissue stress sensitive element not shown) and a means 29 for moving the tissue stress sensitive element 20 (see FIG. 2) into operative engagement with the tissue overlying an artery of interest. Various electrical signals are derived from the tissue stress sensor located within sensor housing 27 and are made available therefrom via conductors within cable 31. These electrical signals carry data which will be used to derive the intra-arterial blood pressure of the wearer of apparatus 21.

Figure 2:
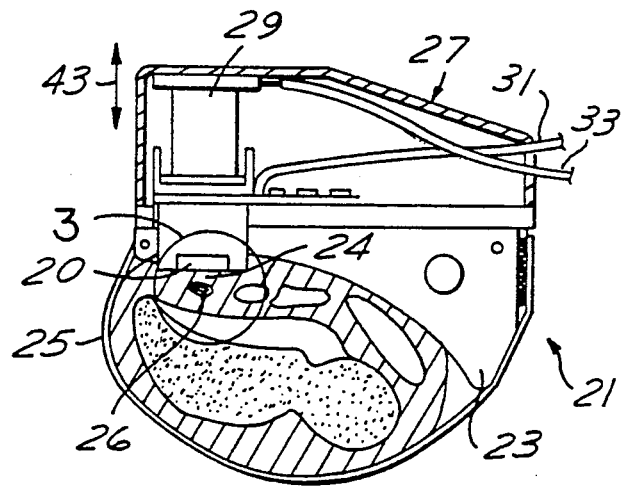
FIG. 2 is a cross-sectional view taken substantially along lines 2—2 of FIG. 1.

Now referring to FIG. 2, sensor housing 27 is mounted to base 23. Within sensor housing 27 is mounted a fluid operated slave bellows 29. Bellows 29 is attached to, at one of its ends, tissue stress sensor 20. As bellows 29 receives a displacement fluid from a source of fluid via tubing 33, it expands downwardly 43 thereby causing tissue stress transducer 20 to engage tissue 24 overlying artery of interest 26.

Figure 3:
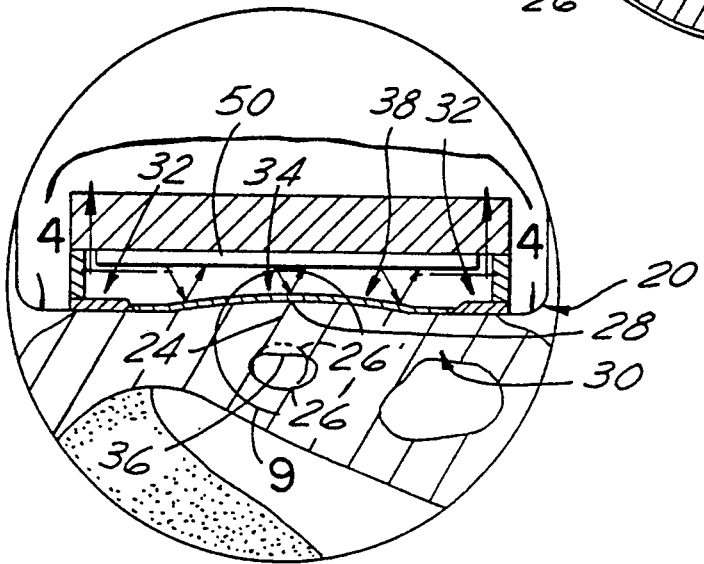
FIG. 3 is an enlarged view of encircled portion 3 of FIG. 2.

Now referring to FIG. 3, tissue stress sensor 20 includes wafer 30 which has a nonresponsive portion 32 and a responsive portion (also denoted as a stress sensitive element or also a diaphragm portion) 34. Nonresponsive portion 32 serves mainly to support responsive portion 34. Under conditions when tissue stress sensor 20 is not being applied against tissue 24, radial artery 26' has a generally rounded opening (or lumen) as depicted at 26'. As wafer 30 of tissue stress transducer 20 is pressed upon tissue 24, radial artery 26' begins to flatten (or applanate) along its top surface 36, thereby causing responsive portion 34 of wafer 30 to deflect slightly inward 38. As the blood pressure within radial artery 26 changes (i.e. pulsates), stress is created in tissue 24 which disturbs the equilibrium between responsive portion 34 of wafer 30 and top surface 28 of tissue 24. This disturbance in equilibrium causes movement between diaphragm 34 of wafer 30 and top surface 28 of overlying tissue 24 (although this movement takes place it is very small due to the stiffness of the diaphragm). Such movement exists until a new equilibrium is established. The ability of diaphragm 34 to move and assume a unique displacement position for a given blood pressure within radial artery 26 forms the fundamental mechanism whereby tissue stress transducer 20 is capable of sensing the intra-arterial pressure of radial artery 26.

Figure 4A:
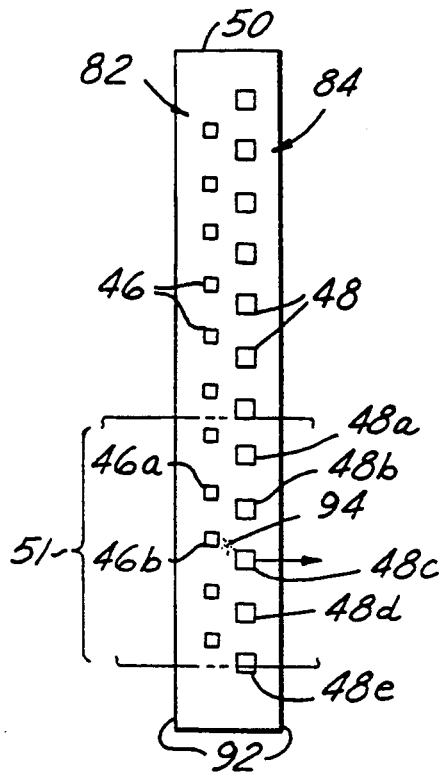
FIGS. 4A and 4B are diagrammatic views of the emitter and detector portions of the semiconductor assembly taken substantially along lines 4—4 of FIG. 3.
Figure 4B:
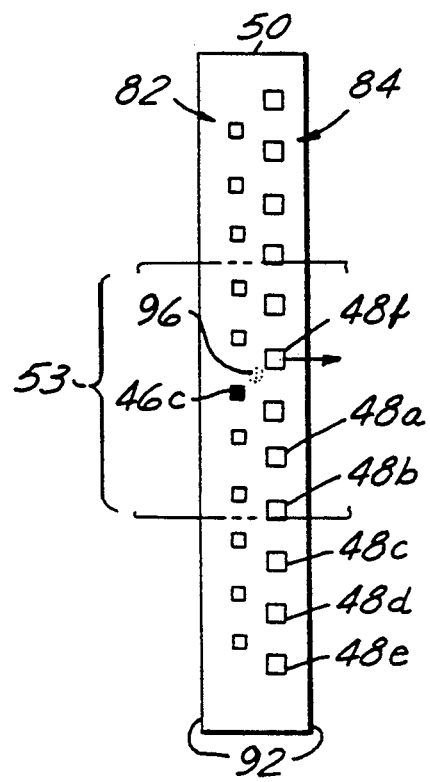

Now referring to FIGS. 4A and 4B, diode array 82 is arranged such that each diode 46 in the array of diodes 82 is generally arranged in a straight row substantially parallel to a long side 92 of electronic substrate 50. Likewise, each receiver 48 in the array of receivers 84 is generally arranged in a straight row which is substantially parallel to a long side 92 of electronic substrate 50. Row of diodes 46 is spaced apart from the row of receivers 48 and each diode 46 is juxtaposed with two receivers 48 such that it lies generally equidistant from its two closest receivers 48. This generally equidistant (or offset) relationship is demonstrated in FIG. 4A by virtue of emitter 46a being generally equidistant from its two closest detector neighbors 48a, 48b. Although this equidistant relationship has some advantages, it is believed that other arrangements between emitters and detectors may also work effectively, including using a single emitter that is scanned across the diaphragm using mechanical or optical steering techniques.

Figure 5:
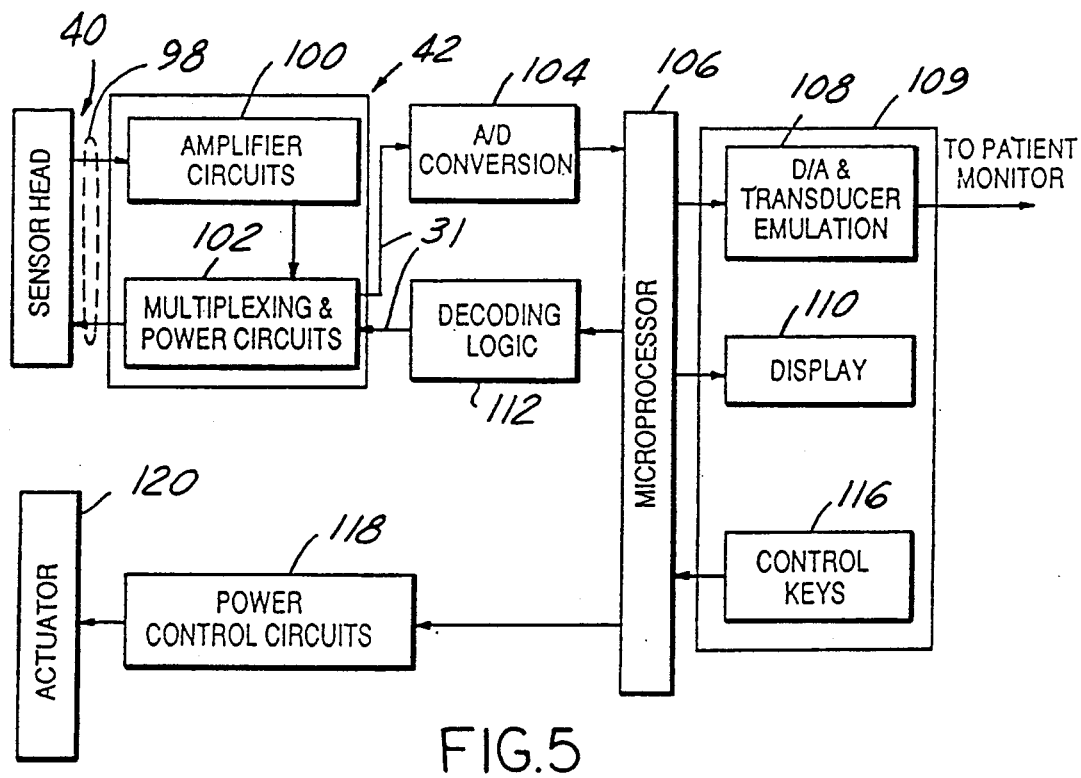
FIG. 5 is an electronic block diagram of the tissue contact stress sensor and associated supporting electronics of the present invention.

Now referring to FIG. 5, sensor head 40 is electronically coupled via multiple communication lines 98 to sensor base portion 42. Sensor base portion 42 provides conversion circuitry 100 to convert the current output signals from the array of detectors 84 to voltage output signals. These voltage signals are sent through multiplexer 102 where they are selectively digitized by A/D converter 104 and passed along to microprocessor 106. Microprocessor 106 performs the error correction spoken of earlier and can also perform various other data compilation or analysis tasks. The blood pressure data can then be sent to any number of outputs such as a digital to analog converter 108 in cases where a continuous analog representation of blood pressure is desirable. Blood pressure data may also be sent to display device 110 where it can provide the user with a continuously updated digital readout of blood pressure. Microprocessor 106 can be programmed to control decoding logic circuitry 112 which in turn activates selected power circuits within multiplexing and power circuits 102.

The user of the system of the present invention can be given certain control options which can be input to microprocessor 106 via control keys 116. Power control circuit 118 can be used to interface microprocessor 106 to any number of mechanical actuators 120 which may be used to respond to various commands from microprocessor 106 in the utilization of sensor 40. For example, a program routine may be used by microprocessor 106 which periodically queries whether sensor head 40 is properly applanating the artery of interest according to a predetermined applanation scheme (such as the schemes disclosed herein). If it is determined that the artery of interest is not properly applanated by wafer 30, microprocessor 106 may activate power control circuit 118 to command actuator 120 to move sensor 20 such that it properly applanates the artery of interest. Other applications may be devised where it is desirable to move, or otherwise control sensor head 20.

Figure 6:
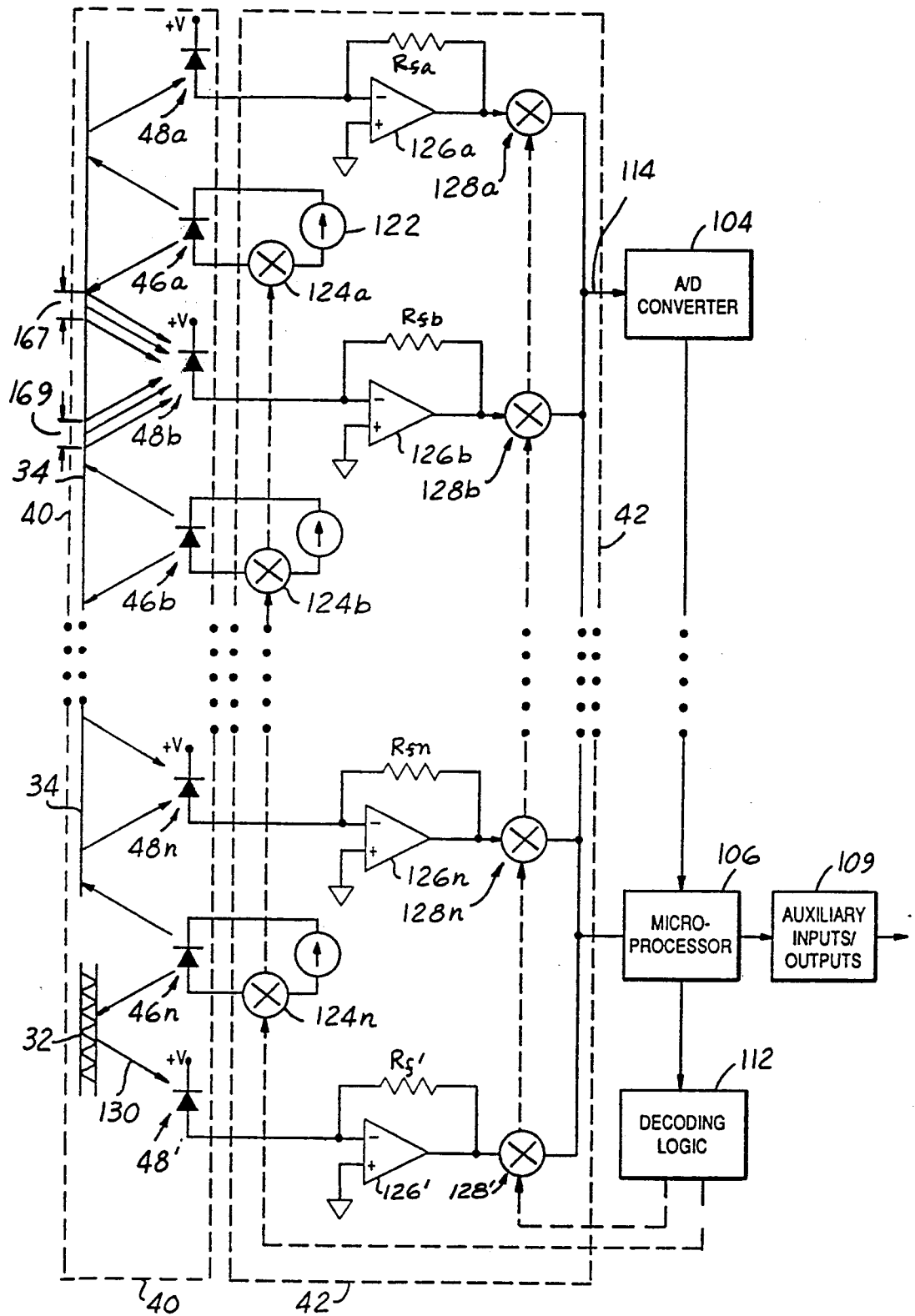
FIG. 6 is a detailed schematic of blocks 40 and 42 of FIG. 5.

Now referring to FIG. 6, sensor head 40 is comprised of a continuous responsive diaphragm portion 34 which reflects light from diodes 46(a-n) and onto receivers 48(a-n). Each diode 46 is fed by current source typified at 122 which can be selectively switched on and off via a respective switch 124(a-n). These switches 124a through 124n are all individually controlled via decoding logic circuit 112. This is the fundamental mechanism whereby each diode 46a through 46n can be selectively activated to determine what portion of diaphragm 34 is best suited to be used to transduce the tissue stress signal. Each receiver 48a through 48n receives a portion of the light reflected from diaphragm 34 and converts this reflected light into an electrical current signal which is converted to a voltage by each receiver's respective converter 126a through 126n. Converters 126a through 126n are configured as current to voltage converters which effect a linear current-to-voltage conversion of the current signal derived from the respective receiver. Current-to-voltage converter circuits are well known to those skilled in the art and, accordingly, will not be discussed in detail here. The output of each converter is made available to its respective switch 128a through 128n. Switches 128a through 128n are controlled via decoding logic 112 which enables microprocessor 106 to select any output from converter 126a through 126n and place it on cable 31 where it is digitized by A/D converter 104.

One detector 48' is adapted to receive light 130 which is reflected from nonresponsive portion 32 of wafer 30. Detector 48' is used to generate a reference signal which will be used by microprocessor 106 to compensate for offset and gain errors due to temperature, aging and other environmental factors.

Figure 7:
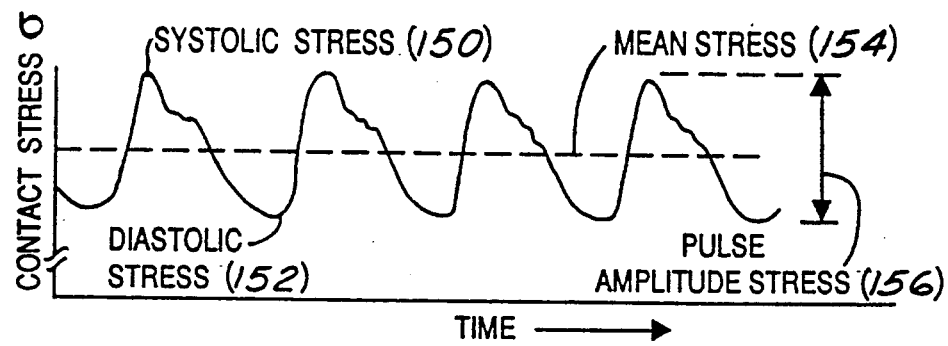
FIG. 7 is a graphic represtation of a typical blood pressure waveform.

Now referring to FIGS. 3, 4A and 4B, 6 and 7, when responsive portion 34 of wafer 30 (responsive portion 34 also known as tissue stress sensitive element or diaphragm) is placed against tissue 24, such that the artery of interest (outlined at 51 of FIG. 4A) is spanned by receivers 48a–48e, each receiver 48a–48e will generate a contact stress signal having the characteristic waveform similar to that shown in FIG. 7. Receivers which are close to center 94 of artery 51 will generate a characteristic waveform of greater magnitude than those at the peripheral edges of artery 51; however, the characteristic contact stress waveform generated by any one of the receivers 48a–48e will exhibit the following, similar characteristics; a point of maximum (or systolic stress) 150 which corresponds to a peak (systolic) blood pressure within artery 26, and a point of minimum (diastolic) stress 152 which corresponds to the diastolic blood pressure within artery 26. Mean stress 154 and pulse amplitude stress 156 are mathematically computed based on the following formula:

$$\sigma_{mean} = \frac{\int_{t_1}^{t_1 + \tau} \sigma(t) \cdot dt}{\int_{t_1}^{t_1 + \tau} dt}, \text{ where } \tau = \text{one heartbeat}$$

Figure 8:
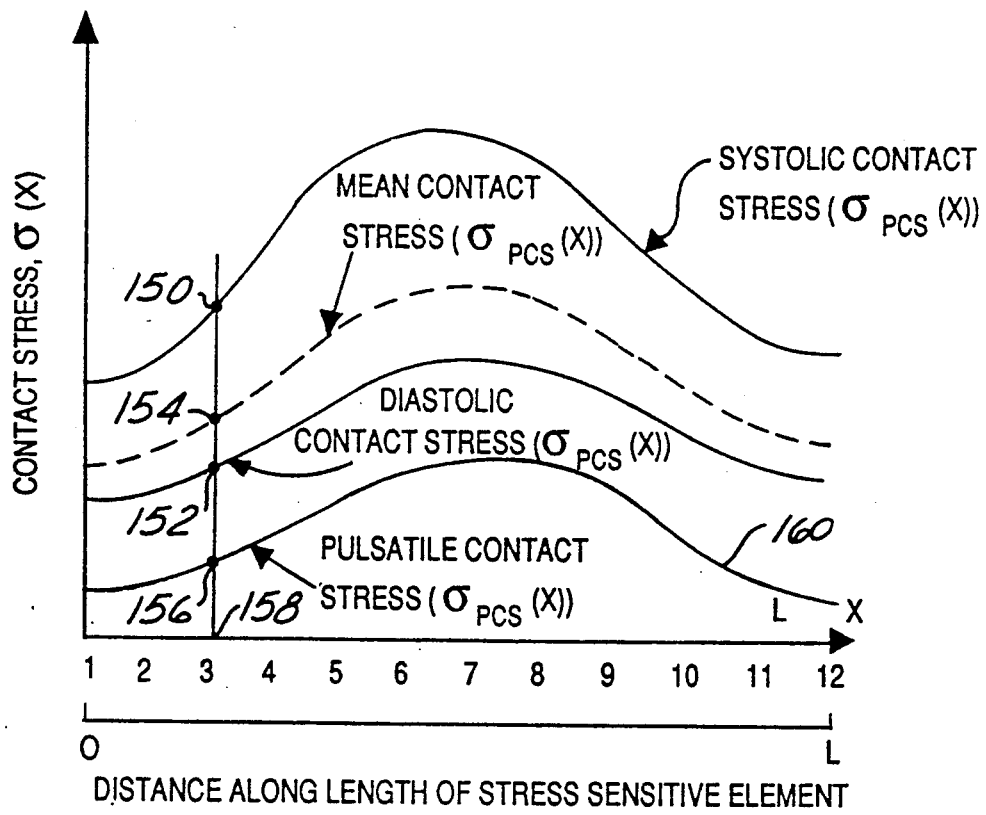
FIG. 8 is a graphical representation of contact stress versus distance along the length of the stress sensitive element.

$\sigma_{pulse\ amplitude} = \sigma_{systolic} - \sigma_{diastolic}$, during one heartbeat Now referring to FIGS. 7 and 8, although contact stress can be plotted as a function of time (as depicted in FIG. 7), it can also be plotted as a function of distance along the length of the stress sensitive element 34 (as shown in FIG. 8). For example, if the characteristic contact stress curve of FIG. 7 represented the stress sensed at location 3 (referenced at 158 in FIG. 8), the characteristic points of systolic stress 150, diastolic stress 152, mean stress 154, and pulse amplitude stress 156 of FIG. 7 would correspond to the similarly marked points in FIG. 8. If the characteristic stress points from all of the locations 1-12 along stress sensitive element are plotted, a contact stress curve resembling that of FIG. 8 would result. The stress information present in FIG. 8 is used in conjunction with the methodologies set forth hereinafter to determine optimum arterial applanation state, to select regions of stress sensor best suited for measuring intra-arterial blood pressure, and for other purposes which are disclosed herein.

Theory of Blood Pressure Tonometry

As was described in conjunction with FIG. 3, a typical tonometric technique for monitoring blood pressure involves positioning a transducer over artery of interest 26 wherein the transducer is pressed against tissue 24 overlying the artery so as to flatten (or applanate) the top surface 36 of artery 26. The transducer may comprise a stress sensitive element 34 which, in turn, may be comprised of a plurality of individual stress sensitive elements or a single, continuous stress sensitive element which is capable of sensing stress along overlapping portions of its length. The stress sensitive element is designed such that it is able to detect (and distinguish between) stresses created along its length. The portion of the stress sensitive element which is typically selected for monitoring blood pressure is that portion which is centered over the applanated portion of the artery inasmuch as this portion is capable of providing the most accurate measure of intra-arterial blood pressure. The portions of the stress sensitive element that do not directly overlie the applanated portion of the artery of interest do not provide as accurate a measure of intra-arterial blood pressure as that provided by the central portions.

In addition to selecting a portion of the stress sensitive element which directly overlies the artery of interest, other factors influence the accuracy to which intra-arterial blood pressure can be measured. One primary factor influencing the accuracy to which intra-arterial blood pressure can be measured is the degree, or extent, to which the artery of interest is applanated at the time the stress sensitive element is measuring tissue stress. Although fairly accurate blood pressure measurements may be made over a wide range of applanation states, it is generally accepted that there exists a substantially unique applanation state which directly produces the most accurate indication of intra-arterial blood pressure. This unique applanation state is commonly known as the optimum applanation state.

Although operating at the optimum applanation state directly produces the most accurate indication of intra-arterial blood pressure, prolonged positioning of the tonometric sensor at that state is known to produce a high degree of patient discomfort. This is primarily due to the tissue displacement associated with achieving and maintaining optimum arterial applanation. In some cases, allowing a tonometric sensor to remain displaced against a patient's tissue (in an optimum applanation mode) for extended periods of time may even cause tissue damage. Thus, it is desirable to find a non-optimum (or off-optimum) applanation state which is comfortable to the patient and which does not cause tissue damage (even if the artery is left in the non-optimum applanation mode for extended periods of time). Ideally, such a state of operation will still yield intra-arterial blood pressure measurements which meet acceptable accuracy standards. The method of the present invention teaches three distinct off-optimum modes of operation.

Much of the prior art, including those references disclosed and discussed herein in the background portion, attempt to relate optimum artery applanation state to hold down pressure (hold down pressure is defined as the pressure applied against the pressure transducer as the transducer is forced against the tissue overlying the artery of interest). It is Applicant's theory that the techniques taught in the prior art are improperly focused and accordingly may not produce results as accurate as the methodologies for determining optimum applanation state as disclosed in co-pending U.S. patent application Ser. No. 07/869,553 filed Apr. 15, 1992, which is hereby incorporated by reference (hereinafter the '553 application). Specifically, while hold down pressure is a parameter which may loosely correlate to artery applanation state, it is believed that there are a number of parameters which may perform this function much better. The methodologies disclosed in the '553 application, set forth a number of applanation state parameters (ASP) which are believed to provide a superior measure (or indication) of actual arterial applanation state. This belief is founded on the fact that the applanation state parameters disclosed in the '553 application are believed to be based upon tonometric principles that are responsive to the physical events which take place when an artery is applanated. These physical events will now be explained in conjunction with FIGS. 3 and 9A–9E.

Figure 9A:
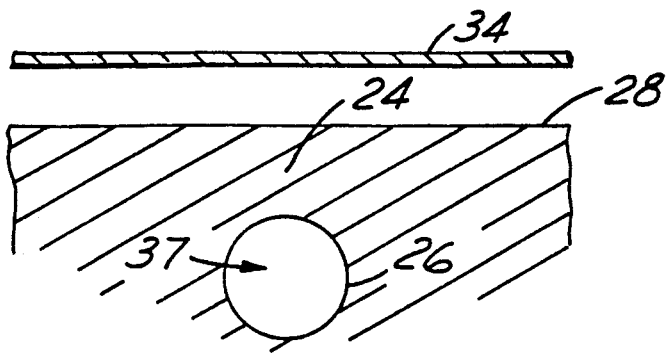
FIG. 9A-9E are diagrammatic representations of the distortion which an artery undergoes when it is applanated (or compressed).
Figure 9B:
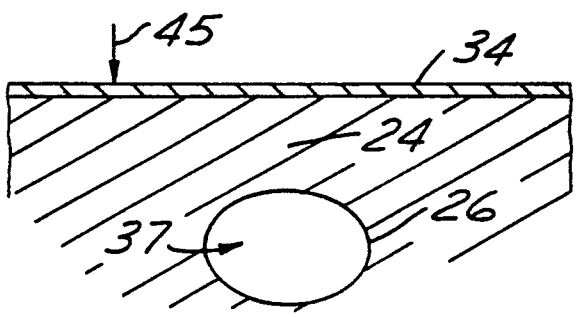
Figure 9C:
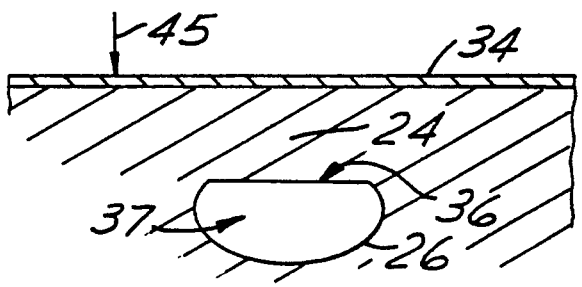
Figure 9D:
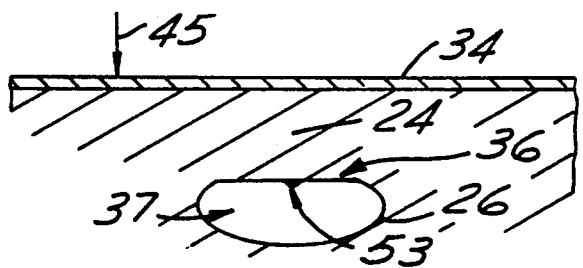
Figure 9E:
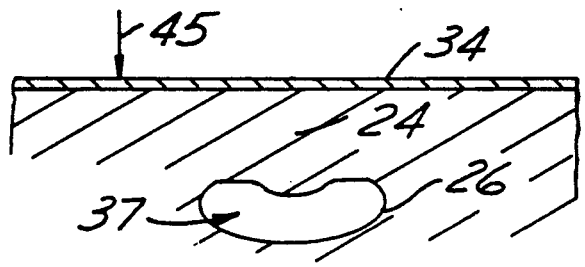

Now referring to FIGS. 3 and 9A–9E, when stress sensitive element 34 is not in contact with top surface 28 of tissue 24, opening (or lumen) 37 of artery 26 maintains a generally circular cross-section (see FIG. 9A). When stress sensitive element is brought in contact with surface 28 of tissue 24 and forced there against, different degrees of artery distortion take place depending, in part, upon the displacement caused by stress sensitive element 34 against surface 28. FIG. 9B–9E depict various stages of deformation of artery 26 as downward displacement 45 increases. As is seen is FIG. 9B, when downward displacement 45 is small, lumen 37 of artery 26 is generally elliptical. As displacement 45 increases beyond that of FIG. 9B to that shown in FIG. 9C, the top surface 36 of artery 26 assumes a generally planar orientation. At this applanation state the localized contact stresses at the tissue surface (over the vessel center) are balanced with the stresses caused by the intra-arterial blood pressure. When the applanation condition depicted in FIG. 9C exists (i.e. top surface 36 of artery 26 is generally planar), artery 26 is said to be in an optimally applanated state. If displacement 45 is increased beyond that shown in FIG. 9C to that shown in 9D, a condition of buckling 53 (or collapsing) occurs in a very small localized region of the vessel wall. In this buckled (or collapsed) state, region 53 is incapable of carrying significant additional localized contact stress. Accordingly, if displacement 45 is increased from that shown in FIG. 9D to that shown in FIG. 9E, the additional contact stresses created along buckled portion 53 are shed (or transferred) to adjacent (not yet buckled) regions. By shedding stress from one buckled region to adjacent non-buckled regions (thereby causing the previously unbuckled regions to then buckle) the stress contour exhibits a non-linear behavior. Many of the methodologies disclosed herein take advantage of this non-linear phenomenon to predict optimum applanation state.

Methods of Continuously Monitoring Blood Pressure

Three different methods (or Modes) of continuously monitoring blood pressure are disclosed herein. Each Mode is briefly set out below along with its associated advantages. Following the brief description of Modes 1, 2 and 3, a detailed description of each Mode follows.

Brief Description of Modes 1, 2, and 3

Mode 1: The first mode involves continuous "servo" applanation adjustment to achieve optimum applanation. In this mode, the servo control mechanism for causing artery applanation is continuously adjusted to position and maintain the tissue stress sensor such that it keeps the underlying artery in an optimum applanation state. In this mode, a composite contact stress waveform extracted from selected portions of the stress sensitive element directly represents the estimated intra-arterial blood pressure waveform. The servo command is an applanation state parameter (applanation state parameters are discussed later) and the error signal for servo control is the difference between optimum applanation state and the existing applanation state. Periodically, the optimum applanation state is re-established and updated. The advantage of this mode is the direct accuracy of the continuous stress waveform because applanation is continuously maintained at the optimum applanation state.

Mode 2: The second mode fixes applanation in the neighborhood of the optimum applanation state but does not attempt to maintain optimum applanation. This mode uses a technique which corrects for the errors associated with operating at an off-optimum applanation state, thereby allowing an accurate assessment of true intra-arterial blood pressure. The applanation servo control mechanism is occasionally adjusted to position the stress sensitive element in the neighborhood of the optimum applanation state. The servo command parameter, error signal, and periodic re-establishment of the optimum applanation point is as previously described for the first mode. The primary advantage of the second mode is that it requires less frequent applanation control actuations than that required by the first mode. This has the associated advantage of reducing the power requirements associated with driving the servo controller.

Mode 3: The third mode operates the stress sensitive element to applanate the artery of interest to a small fraction of the optimum applanation state. The data generated from the stress sensitive element is corrected to accurately indicate true intra-arterial blood pressure. The servo control mechanism is occasionally adjusted to re-position the stress sensitive element at a small fraction of the optimum applanation state. Although the stress sensitive element is positioned far below the optimum applanation state, accurate, continuous intra-arterial blood pressure measurements are obtained because the data extracted from the stress sensitive element is corrected thereby compensating for the errors associated with collecting stress data at an off-optimum applanation state. Other aspects of the third mode of operation are identical to those discussed in conjunction with the first and second modes. The primary advantage of the third mode is improved patient comfort and the reduced risk of localized, tissue damage. This advantage is made possible by the reduced tonometer compression against the tissue for most of the monitoring time.

Mode 1: Continuously Adjust to Optimum Applanation State

Figure 17:
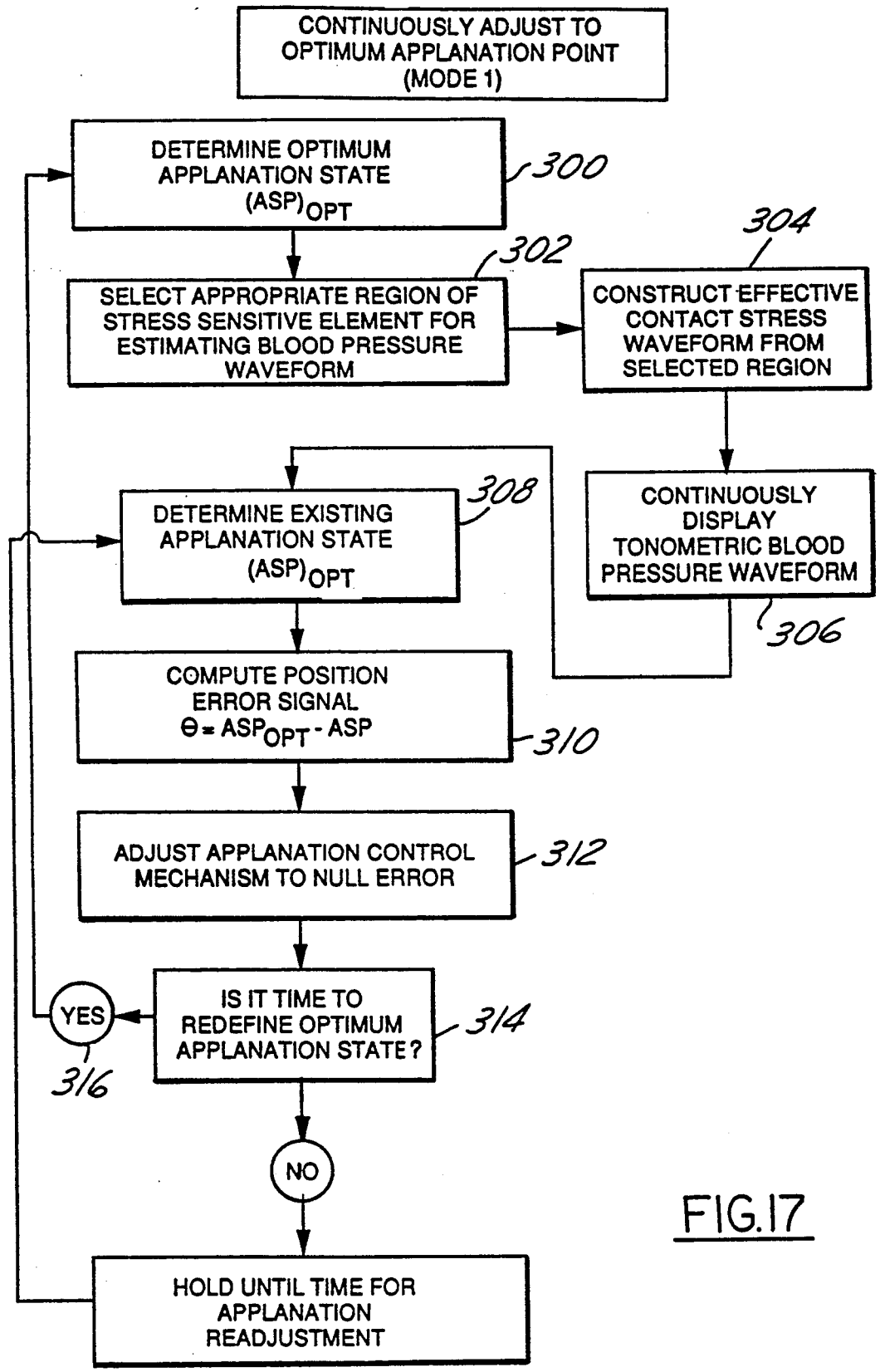
FIG. 17 is a logic flow diagram showing a first mode of operation for continuously monitoring intra-arterial blood pressure.

Now referring to FIGS. 2, 3, 8, 10, and 17, each of the three methods herein disclosed for continuously monitoring intra-arterial blood pressure utilize similar methods for determining optimum applanation state 300 (see FIG. 17). Twelve different preferred methods for determining optimum applanation state 300 are disclosed in co-pending '553 application. For the sake of completeness, the first of the 12 different methods set out in the above-reference co-pending application will now be explained.

General Discussion of Determining Optimum Applanation State

Figure 10:
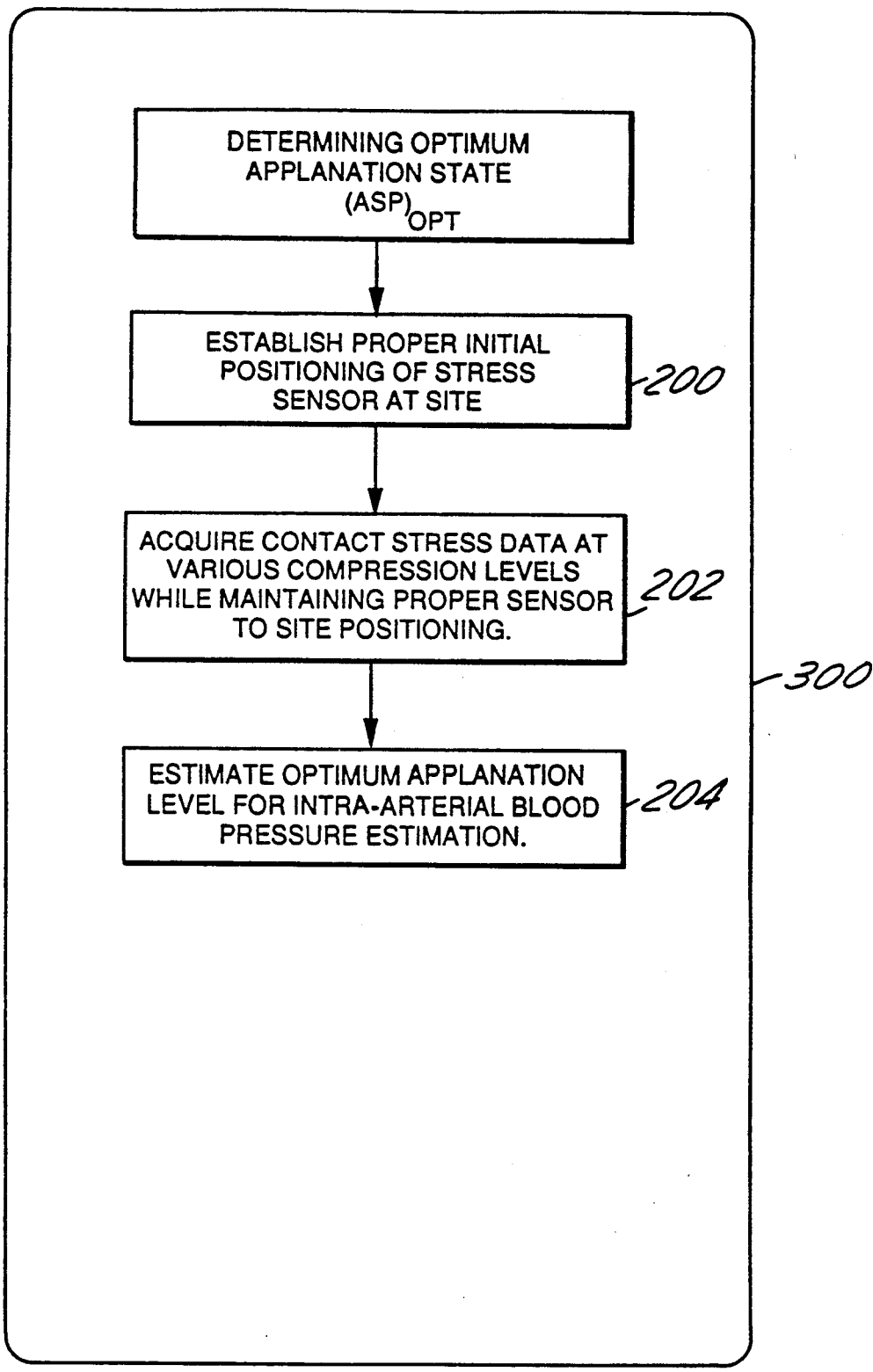
FIG. 10 is a block diagram showing the logic flow associated with determining the optimum applanation state.

Now referring to FIGS. 3 and 10, preparation for monitoring intra-arterial blood pressure begins by establishing proper initial positioning of stress sensor 20 (see FIG. 3) on the user's wrist or other appropriate site 200. Once proper, initial positioning is established 200, stress sensor 20 collects contact stress data 202 (see FIG. 8). Once this stress data has been collected, applanation (or servo) means 29 (see FIG. 2) moves sensor 20 thereby establishing a new applanation level. This process of collecting stress data continues for each unique applanation state. The movement of applanation means 29 can be accomplished in a step-wise fashion or in a continuously varying fashion. Once applanation means 29 has completed its applanation cycle, systolic, diastolic, pulsatile, and waveform mean contact stresses are derived as functions of position along the stress sensitive element (see FIG. 8) and also as functions of applanation state. From the acquired contact stress data, one or more optimum applanation methodologies are utilized for determining the optimum applanation compression level for intra-arterial blood pressure estimation 204. Once the optimum arterial compression level is determined, certain portions of the data which were collected during the optimum applanation level are selected for computing special correction factors and also computing diastolic and pulsatile applanation scaling factors.

Defining and Utilizing Applanation Optimization Parameters and Applanation State Parameters When implementing methodologies for non-invasively determining optimum applanation state, it is helpful and convenient to develop various classes of functions. Two particular classes of parameters (or functions) disclosed herein are Applanation Optimization Parameters and Applanation State Parameters. Applanation Optimization Parameters (AOP) are parameters derived from the stress sensor signals which provide guidance in selecting the optimum artery applanation state. The Applanation State Parameters (ASP) are parameters which indicate the degree to which the artery has been flattened or distorted as it is acted upon by tissue stress sensor 20. When attempting to determine optimum applanation state, it is helpful to generate a relationship between the Applanation Optimization Parameters and the Applanation State Parameters. Generally the methods of the present invention do this by making the Applanation Optimization Parameter AOP a function of the Applanation State Parameter AOP-(ASP). This function is then analyzed for some characteristic trait, the occurence of which indicates the optimum applanation state. In the sample method set forth herein to determine optimum applanation state, one AOP is defined and then used for determining the "best" or optimum artery applanation state and the selected ASP is adjusted until a preferred or optimum AOP(ASP) is found.

One example of an Applanation State Parameter is a parameter which relates to the displacement of the stress sensor as it is moved against the tissue overlying the artery of interest. For example, a displacement of 10 mils (one mil is equal to one-one thousandth of an inch) may receive an Applanation State Parameter value of 1, 20 mils equals an Applanation State Parameter value of 2, etc. Another possible Applanation State Parameter is simply to measure the force against tissue stress sensor 20 (see FIG. 2) as it is displaced into tissue 24 by moving means (or bellows) 29. Still another applanation state parameter may be derived by calculating (for a given applanation state) the average contact stress across the entire length of the stress sensitive element. This method may include applanating an artery to a first state and then, while held in that state, calculating the average contact stress across the entire length of the stress sensitive element. This method would then be repeated over a range of applanation states. Mathematically, this method is expressed as follows:

$$AASI_1 = \sigma_{AVG(AAS1)} = \frac{\int_0^L \sigma(x)_{AAS1}}{\int_0^L dx}$$

where:

$\sigma AVG(AAS_1)$ = average stress value across the length of the stress sensitive element while the artery of interest undergoes the first artery applanation state
$AAS_1$ = First Artery Applanation State
$AASI_1$ = First Artery Applanation State Index
$\sigma(x)_{AAS1}$ = stress data sensed by stress sensing element at location x while the artery of interest undergoes the first artery applanation state
x = location along the length of stress sensitive element
O, L = limits of integration across the length of stress sensitive element Preferred Applanation State Parameters ASP The following list sets forth five applanation state parameters which are believed to be unique (and useful) measures (or indicators) of the actual degree or state of artery applanation. As later disclosed herein, the use of the applanation state parameters (either individually or combined) to form a composite indicator representing state of artery applanation is a key in forming functional relationships which are used in the methodologies to determine optimum arterial applanation. Several additional ASP's are set forth in earlier referenced co-pending '553 application.

A. AVERAGE DIASTOLIC CONTACT STRESS FACTOR (STRESS COLLECTED in PASSIVE REGIONS REMOTE from VESSEL). [1]

(1) Average tissue diastolic contact stress collected from the most passive regions of tissue (most remote from vessel).

B. DIASTOLIC CONTACT STRESS DISTRIBUTION BREADTH FACTOR. [1], [2]

(1) Average tissue diastolic contact stress (across full length of stress sensitive element) divided by tissue diastolic contact stress at maximum tissue pulsatile stress location, or (2) Average tissue diastolic contact stress in passive tissue regions (remote from vessel) divided by average tissue diastolic contact stress in active tissue regions (over vessel), or (3) Average tissue diastolic contact stress (across full length of stress sensitive element) divided by average tissue diastolic contact stress over a select portion of the stress sensitive element having maximum tissue pulsatile stress.

C. AVERAGE DIASTOLIC CONTACT STRESS (STRESS COLLECTED OVER ENTIRE LENGTH of STRESS SENSITIVE ELEMENT). [1]

D. NORMALIZED or DIMENSIONLESS AVERAGE DIASTOLIC CONTACT STRESS FACTOR (STRESS COLLECTED in PASSIVE REGIONS REMOTE from VESSEL). [1]

(1) Ratio of the index computed by method A(1) above at applanation state of interest to that index method computed at applanation state for maximum pulsatile contact stress, or (2) Ratio of the index computed by method A(1) above at applanation state of interest to that same index method computed at any particular characteristic applanation state selected for the normalization process.

E. NORMALIZED or DIMENSIONLESS AVERAGE DIASTOLIC CONTACT STRESS FACTOR (STRESS COLLECTED OVER ENTIRE LENGTH of the STRESS SENSITIVE ELEMENT). (1)

(1) Ratio of the index computed by method C above at applanation level of interest to index C above computed at applanation level for maximum pulsatile stress, or (2) Ratio of the index computer by method C above at applanation level of interest to index C above computed at any particular characteristic applanation state selected for the normalization process.

Notes: (1) These Applanation State Parameters are Especially Important in that They Utilize Tissue Contact Stress Data Already Being Utilized from the Stress Sensor Itself and Do Not Require Data from a Separate Sensor or Transducer.

(2) This Application State Parameter is Unique in that It is a Measure of the Change in "Shape" of the Contact Stress Distribution Profile (along the Length of the Stress Sensitive Element) as One Changes the State or Level of Vessel Applanation. It is a Dimensionless Index.

Detailed Discussion of Optimum Applanation Method 1

Now that the concept of Applanation Optimization Parameters and Applanation State Parameters has been introduced, it is appropriate to explain how the AOP's and the ASP's are used to determine the optimum applanation state. One such method of determining optimum applanation state will now be discussed.

The optimum applanation method herein disclosed utilizes the Pulsatile Stress Parameter (PPAR) to determine the optimum applanation state of the artery of interest. The Pulsatile Stress Parameter PPAR is defined as the average difference between the systolic contact stress $\sigma_{SCS}(x)$ and diastolic contact stress $\sigma_{DCS}(x)$ in the region or regions of the stress sensitive element having the greatest pulse energy content. Mathematically, PPAR is defined as follows:

$$PPAR = \frac{1}{c-b} \int_b^c (\sigma_{SCS}(x) - \sigma_{DCS}(x)) \cdot dx$$

Figure 11:
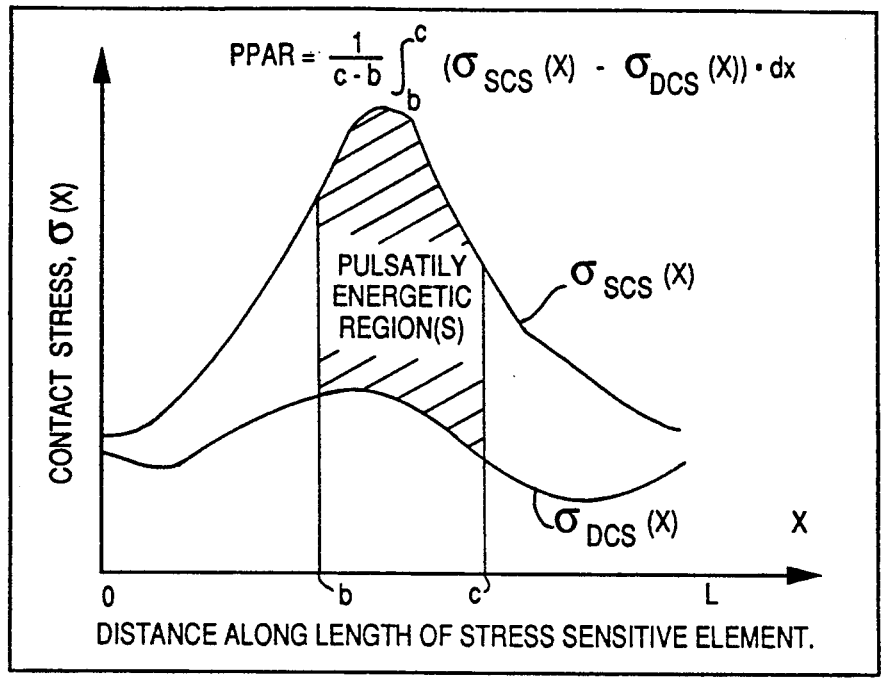
FIG. 11 is a graphical representation of the steps for calculating the PPAR parameter.

A graphical representation of the method of calculating PPAR is shown in FIG. 11. It is important to note that the PPAR parameter is calculated between bounds b and c. Preferably bounds b and c represent the region having the greatest pulse energy content. Other methods of determining bounds b and c may work equally as well. Methods of determining the bounds for the region of greatest pulse energy content are found later in this disclosure under the subheading Methods of Determining Limits of Integration When Calculating PPAR.

Because the following relationship exists:

$$\sigma_{SCS}(x) - \sigma_{DCS}(x) = \sigma_{PCS}(x)$$

(where $\sigma_{PCS}(x)$ is the pulsatile contact stress), PPAR as defined in FIG. 11 is equivalently expressed as follows:

$$PPAR = \frac{1}{c-b} \int_b^c \sigma_{PCS}(x) \cdot dx$$

Figure 12:
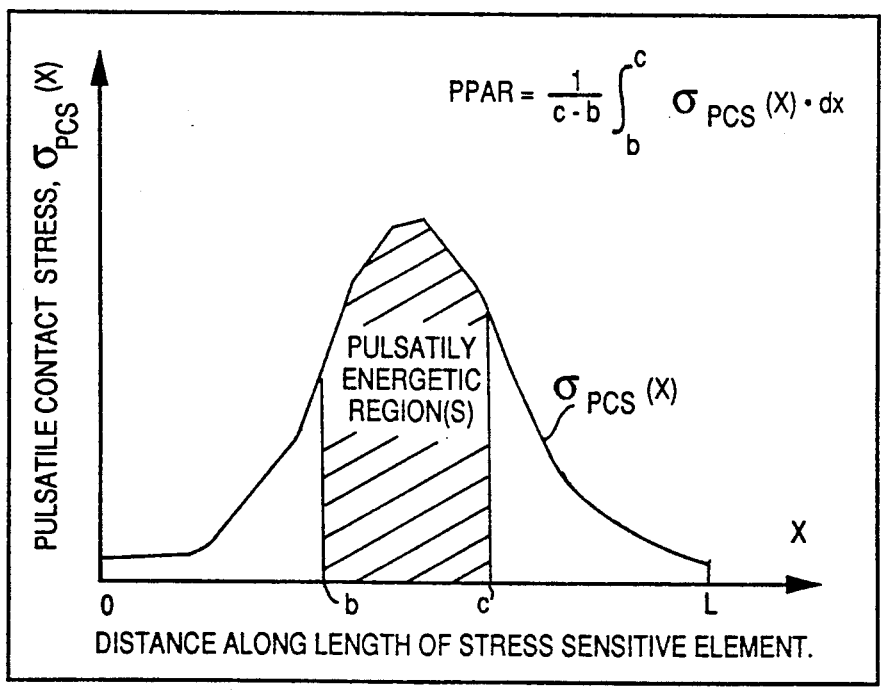
FIG. 12 is a graphical representation of an equivalent method of calculating the PPAR parameter.

This equivalent manner of calculating PPAR is graphically depicted in FIG. 12.

Figure 13:
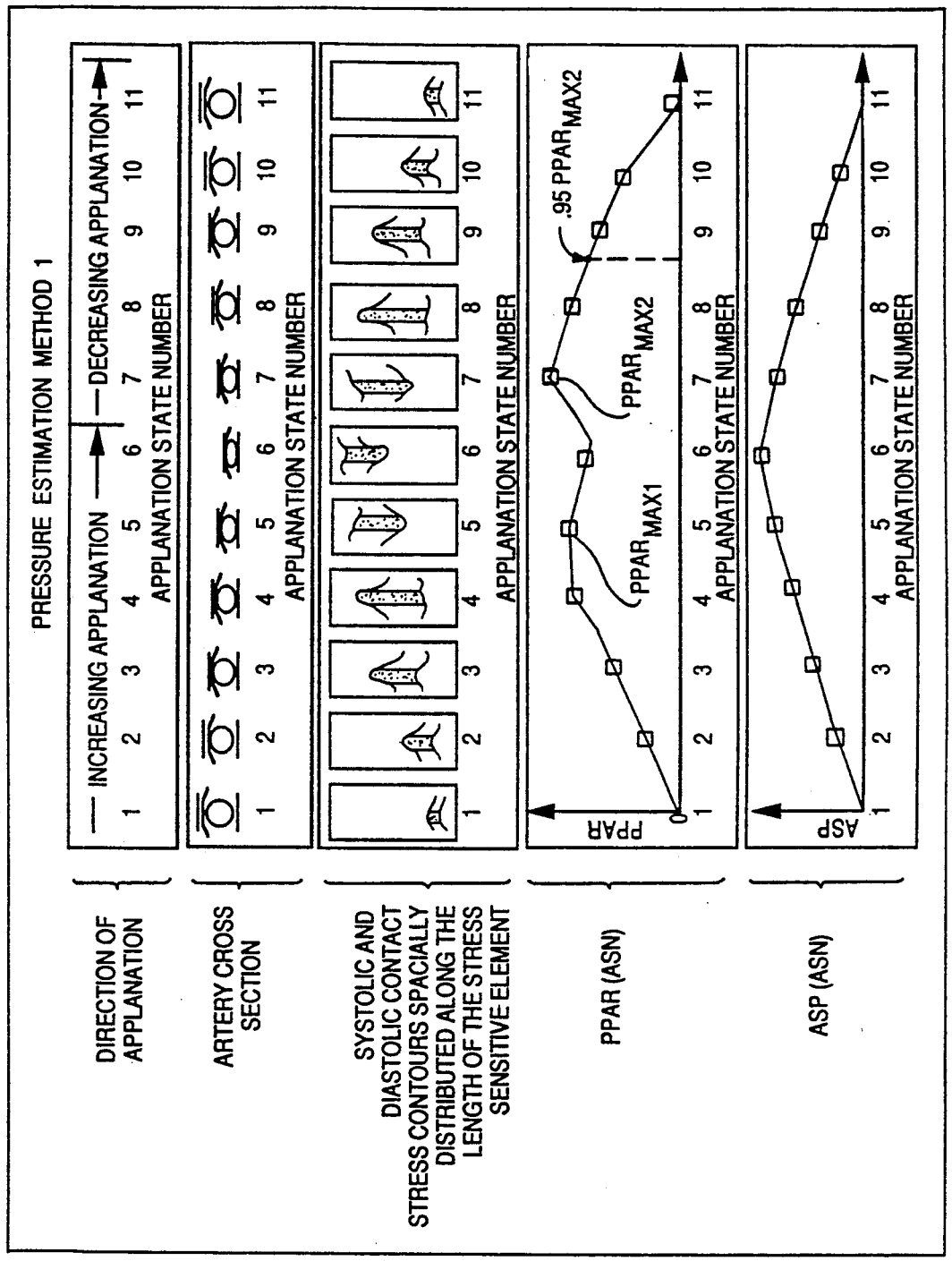
FIG. 13 is a combined graphical and diagrammatical representation of the method steps utilized in generating the PPAR parameter as a function of ASP.

Now referring to FIG. 13, the implementing of Method 1 includes the following steps:

1) Using the artery applanation control mechanism 29 (see FIG. 2) to adjust the state of artery applanation through a broad range of applanation states (the applanation states are represented by the applanation state numbers shown in FIG. 13) while acquiring contact stress data (as depicted in FIG. 11) at various applanation states.

2) At each applanation state, computing PPAR and computing ASP. The preferred ASP for Method 1 is either displacement (as set forth in paragraphs C and D in the previous section entitled Preferred Applanation State Parameters) or the average diastolic contact stress computed as follows:

$$\sigma_{DCSAVG} = \frac{1}{L} \int_0^L \sigma_{DCS}(x) \cdot dx$$

3) Creating a function relating PPAR to the selected ASP (i.e. PPAR (ASP)).

4) Defining the optimum applanation state to be when PPAR (ASP) reaches 95% of its maximum value.

5) Calculating the optimum applanation state as follows:

$$PPAR_{opt} = PPAR_{max} \times 0.95$$

In implementing the above-discussed applanation optimization process, the optimum applanation state is found by first increasing the arterial applanation until the PPAR reaches a first maximum PPARmax$_1$ and then diminishes by a specified fraction of the maximum value. Next, the applanation is reduced, and typically, PPAR will increase temporarily to a second maximum PPARmax$_2$. Upon further reduction of applanation, when PPAR reaches approximately 95% of the second maximum, and conditions are met for estimation of true arterial blood pressure. This process is shown in the graph of PPAR(ASN) found in FIG. 13. Alternatively, the estimation can be made at other points including the interval prior to PPARmax$_1$ in which applanation is increasing.

As discussed above, and as evidenced in the graph of PPAR(ASN) found in FIG. 13, stress data is collected during the interval of increasing applanation as well as during the interval of decreasing applanation. Although stress data collected during either or both of the intervals may be used for computing the applanation optimization parameter as well as the applanation state parameter, the preferred method is to use the stress data which is collected during decreasing applanation. This is the preferred method because it is believed that stress data collected during the decreasing applanation interval more closely predicts the actual intra-arterial blood pressure than that data collected during the increasing applanation interval.

Although 95% has been disclosed herein as the optimum fraction to use when determining optimum arterial applanation, a preferred method of determining the exact optimum fraction is to empirically collect, from statistically significant classified populations, data in which tonometric values versus automatic cuff or invasive blood pressure values are statistically correlated. The preferred fraction may vary depending on certain factors such as whether applanation is increasing/decreasing, sex (and age) of person being examined, etc. Initial studies indicate that results are more uniform when applanation is decreasing and therefore this is the preferred mode of operation when collecting contact stress data.

Methods of Determining Limits of Integration When Calculating PPAR

A preferred method for determining the spatial limits of integration (b and c) employs the concept of energy transfer. This concept is based on the theory that the energy coupling between the artery of interest and the contact stress element is greatest in the immediate vicinity of the artery of interest. The boundaries of this high energy region are used to define the integration limits (b, c). Thus, one can determine the limits of integration (b, c) by determining which portion (or portions) of the stress sensitive element is in receipt of the maximum contact stress energy. The methods of the present invention use the square of the contact stress values to obtain a measure of contact stress energy and thereby construct a relationship between contact stress energy and position along the length of the stress sensitive element.

Figure 14:
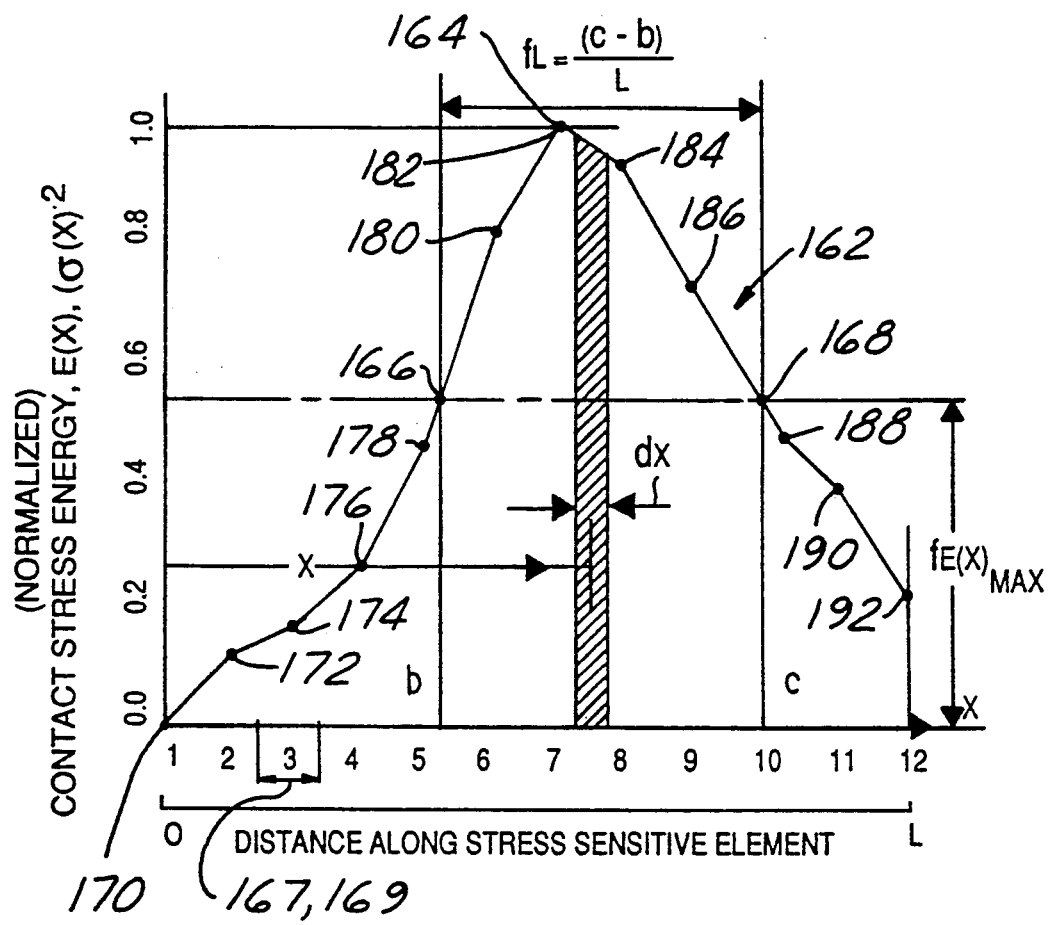
FIG. 14 is a graph showing contact stress energy as a function of distance along the stress sensitive element.

The above-referenced methodology is demonstrated graphically in FIG. 14. To implement this method of finding the limits of integration (b, c), one must first select one of the stress contours as set out in FIG. 8. While any one of the four stress contours may perform satisfactorily when implementing this method, the pulsatile stress energy contour is preferred. Thus, after obtaining pulsatile stress values across the length of the stress sensitive element (as depicted in graph 160 of FIG. 8), each pulsatile stress value (exemplified at 156) is squared thereby relating pulsatile contact stress energy $E(x)$ to distance along the stress sensitive element. This method is in stark contrast with the approach of the prior art of simply calculating various parameters over the entire length of the stress sensitive element. The reason this approach is believed to be superior over that of calculating parameters of the full length of the stress sensitive element is because this method ignores the portions along the stress sensitive element which make only a minor contribution to the function being examined. Accordingly, this approach eliminates the influence of portions of the function which are not centered over the artery of interest. Two methods will now be discussed, each of which can be used for determining the region (or regions) over which the PPAR parameter can be computed.

Percent of Maximum Method

The first method for determining the limits over which the centroid of a selected function will be computed, includes using only those regions of the select function which exceed a predetermined selected threshold fraction of the maximum value of the function. For example, applying this method to the contact stress energy function as set out in FIG. 14, first, maximum 164 is determined and then a predetermined portion of the maximum is taken. Suppose, for example, that 50 percent of maximum 164 will serve as the threshold fraction. This fraction intersects the contact stress energy function at points 166 and 168 thereby forming the limits (b, c) over which the PPAR function will be calculated. It is important to note that although the function depicted in FIG. 14 is shown having only one contiguous region which satisfies the percent of maximum condition, it is probable that under actual use conditions, several discontiguous regions will satisfy the percent maximum condition. In this case (i.e., when discontinuous "optimum" regions exist, each of which meet the "optimum" cirteria), then calculate the PPAR function over each of the discontiguous regions of the energy curve which satisfy the percent of maximum condition (as if they were actually adjacent) leaving out the intervening region of the sensor.

Percent of Stress Sensitive Element Method

The second method of determining limits (b, c) includes using selected portions of greatest magnitude of the contact stress energy function that have a cumulative total length equal to a predetermined percentage of the total length of the stress sensitive element. This method can be easily explained in conjunction with FIGS. 6 and 14. As seen in FIG. 6, sensing diode 48b is capable of sensing deflections along stress sensitive element 34 along regions or portions 167, 169 of stress sensitive element 34. Thus, when viewing point 174 of FIG. 14 (which we are assuming is the representative output of detector 48b), we see that this output does not represent a point along stress sensitive element 34, but rather represents the composite stresses served along continuous portion 167 and 169 of stress sensitive element 34. Accordingly, each output value 170 through 192 corresponds to one or more portions along stress sensitive element 34. Thus for example, in applying the present method of determining limits (b, c) from the contact stress energy function disclosed in FIG. 14, the following steps are followed:

1. Ordering the contact stress energy values 170–192 according to magnitude.
2. Associating each of the contact energy stress values with a predetermined segment length, or lengths along the length of the stress sensitive element (e.g. stress value 174 is associated with lengths 167 and 169).
3. Selecting the contact stress energy values of greatest magnitude as previously ordered and totaling the lengths of each predetermined segment that is associated with the selected contact stress energy values.
4. Setting n equal to the number of contact stress energy values selected when the cumulative predetermined segment lengths (as totaled in step 3) exceed a predetermined percentage of the length of the stress sensitive element.
5. Computing the centroid of contact stress energy using only those n segments selected.

As with the previously disclosed percent of maximum method of determining boundaries (b, c), this method may produce selected regions which are noncontiguous. Nonetheless, the disclosed method is applied identically regardless of whether the regions are contiguous or non-contiguous.

This concludes the detailed explanation of one method for determining (and quantifying) optimum applanation state 300. Additional methods are set out in the '553 application.

Selection of Appropriate Stress Sensitive Element Region for Estimating Blood Pressure Waveform Now referring to FIG. 17, once the optimum applanation state is defined 300, the systolic and diastolic contact stress contours which correspond to the optimum applanation state are analyzed to determine the best physical location (or locations) along the length of the stress sensitive element from which intra-arterial blood pressure may be estimated 302. There are two preferred techniques for estimating which location or locations along the stress sensitive element are best suited for estimated intra-arterial pressure. These two techniques—Estimating Technique A and Estimating Technique B—will now be explained in detail in conjunction with FIGS. 13, 15 and 16.

Estimating Technique A

Figure 15:
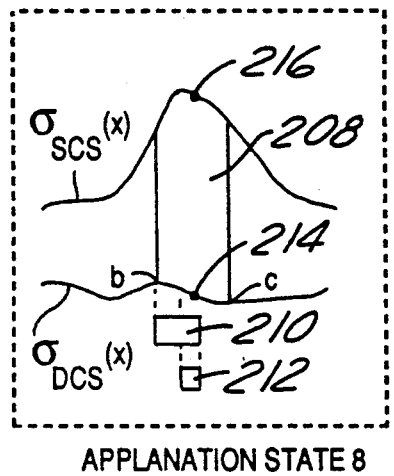
FIG. 15 is a graphical representation of Estimating Technique A for estimating intra-arterial blood pressure from contact stress data.

Now referring to FIGS. 13 and 15, assume for the moment that when the PPAR parameter was calculated, and optimized, the result of that optimization was that applanation state 8 (see FIG. 13) was the optimum applanation state. The systolic contact stress waveform $\sigma_{SCS}(x)$ and the diastolic contact stress waveform $\sigma_{DCS}(x)$, as they exist for applanation state 8, are shown in FIG. 15. In implementing Technique A, we first chose a subregion 210 of the defined area having maximum pulse energy 208. Subregion 210 will typically be two-thirds of the width of region 208. Subregion 210 will be chosen as that fraction of the width of 208 which has the greatest pulsatile contact stress $\sigma_{PCS}(x)$. Then, a yet smaller fraction 212 (typically one-half of the width of subregion 210) is determined by finding the subregion within region 210 having the smallest diastolic contact stress $\sigma_{DCS}(x)$. The diastolic contact stress point 214 and the systolic contact stress point 216 corresponding to subregion 212 is then used as the estimate of intra-arterial blood pressure systole and diastole points respectively. If, on the other hand, a continuous wave is desired, the location or locations along the stress sensitive element corresponding to region 212 can be used to furnish a continuous representation of intra-arterial blood pressure.

Estimating Technique B

Figure 16:
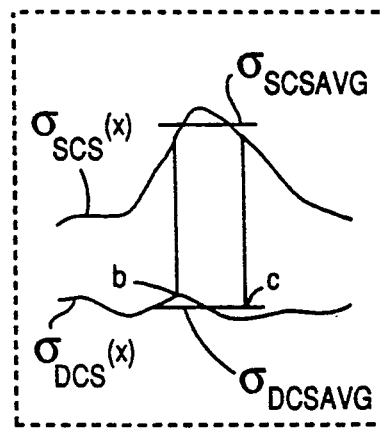
FIG. 16 is a graphical representation of Estimating Technique B for estimating intra-arterial blood pressure from contact stress data.

Now referring to FIGS. 13 and 16, assuming that applanation state 8 is determined to be the optimum applanation state after applying the PPAR criteria, Technique B estimates the region along the stress sensitive element best suited for estimating intra-arterial blood pressure to be that region that generates a systolic and diastolic blood pressure point which is statistically closest to the average diastolic contact stress $\sigma_{DCSAVG}$ and the average systolic contact stress $\sigma_{SCSAVG}$. The mathematical formula for computing $\sigma_{DCSAVG}$ is as follows:

$$\sigma_{DCSAVG} = \frac{1}{b-c} \int_b^c \sigma_{DCS}(x) \cdot dx$$

The mathematical formula for computing $\sigma_{scsavg}$ is as follows:

$$\sigma_{SCSAVG} = \frac{1}{b-c} \int_b^c \sigma_{SCS}(x) \cdot dx$$

Thus, under this approach, each portion along the stress sensitive element (between bounds b and c) is examined to determine which portion is generating a diastolic and systolic pressure point which is statistically closest to $\sigma_{DCSAVG}$ and $\sigma_{SCSAVG}$. There are many statistical methods such as the least squares method known to those skilled in the art for determining this type of "best fit" analysis.

Construction of Effective Contact Stress Waveform from Selected Regions

Now referring to FIG. 17, the contact stress waveform to be utilized 304 is preferably constructed by using one of the two following methods.

First Method of Constructing the Contact Stress Waveform

Under this first method, a composite (or effective) contact stress waveform $\sigma_{EFF}(t)$ is constructed using a combination of individual waveforms extracted from sampled locations in the selected region or regions of the stress sensitive element to represent the true intra-arterial blood pressure waveform (see Estimating Techniques A and B disclosed earlier for techniques for determining selected regions of the stress sensitive element). The contact effective stress waveform is constructed using a simple spatial average of all (or some) of the sampled waveforms from the selected region:

$$\sigma_{EFF}(t) = \frac{1}{N} \sum_{i=1}^{N} \sigma_i(t)$$

where:

$\sigma_{EFF}(t)$ = Effective contact stress waveform for the selected region $\sigma_i(t)$ = Contact stress waveform for one of the sampled locations in the stress sensitive element N = Number of sampled locations in the selected region t = Time Second Method for Constructing Contact Stress Waveform The second method for constructing the effective contact stress waveform is a variation of the first method. In the second method, the contact stress waveform is constructed using a weighted spatial average of all (or some) of the sampled waveforms from the selected region using an appropriately selected weighting function with each sampled waveform. With the second method, the contact stress waveform from a specific sampling point within the selected region (as disclosed earlier in Estimating Techniques A and B) is used as a starting basis. To this waveform, correction factors of a spatial type are applied to adjust the waveform to be consistent with the effective diastolic and pulsatile contact stresses for the region known to approximate the true intra-arterial diastolic and pulsatile pressure. The preferred sampling point location used to extract the waveform to be used as the starting basis could be that sampling point (bounded by b and c) which yields the largest pulse stress value. Alternatively, it could be the sampling point that yields diastolic and pulse stress values that are statistically closest to the diastolic and pulse stress values established for the selected region of the stress sensitive element according to the methods set forth under earlier disclosed Estimating Technique A and Estimating Technique B.

The correction factors employed in the second method for constructing the contact stress waveform are calculated as follows:

1. For a given beat of interest, establish the effective diastolic $(\sigma^*_{DIAS})_{EFF}$ and pulse $(\sigma^*_{PULSE})_{EFF}$ contact stresses associated with the selected regions of the stress sensitive element:

$$(\sigma^*_{DIAS})_{EFF} = \frac{1}{b-c} \int_b^c \sigma^*_{DIAS}(x) \cdot dx \qquad (1)$$

-continued $$= \frac{1}{N} \sum_{i=1}^{N} (\sigma^*_{DIAS})_i \quad (2)$$

$$(\sigma^*_{PULSE})_{EFF} = \frac{1}{b-c} \int_b^c \sigma^*_{PULSE}(x) \cdot dx \quad (3)$$

$$= \frac{1}{N} \sum_{i=1}^{N} (\sigma^*_{PULSE(i)}) \quad (4)$$

where:
$\sigma^*_{DIAS}(x)$ = diastolic stress
x = location along stress sensitive element
b, c = limits of integration
i = denotes one of the sampling points within the selected region of the stress sensitive element.
N = is the total number of sampled points within the selected region of the stress sensitive element.
Note that formulas (1) and (2) are meant to be equivalent forms of the same expression and either one maybe used to derive $(\sigma^*_{DIAS})_{EFF}$. The same comment holds for formulas (3) and (4).

2. For this same beat of interest, select a specific sampling point $\sigma_{S.P.}(t)$ within the selected region to be used to generate the "basis waveform" and establish the diastolic and pulse contact stress for that specific sampling point:
$(\sigma^*_{DIAS})$ S.P.
$(\sigma^*_{PULSE})$ S.P.

3. Compute the spatial correction factors m,b for the "basis waveform" where:

$$m = \frac{(\sigma^*_{DIAS})_{EFF} - (\sigma^*_{PULSE})_{EFF}}{(\sigma^*_{DIAS})_{S.P.} - (\sigma^*_{PULSE})_{S.P.}}$$

$$b = [(\sigma^*_{PULSE})_{EFF} - (\sigma^*_{PULSE})_{S.P.}] \cdot m$$

4. The spatially corrected effective contact stress versus time waveform $\sigma_{EFF}(t)$ associated with the selected region to be displayed $\sigma_{S.P.}(t)$ is then constructed as follows:

$$\sigma_{EFF}(t) = \sigma_{S.P.}(t) \cdot m + b$$

After the contact stress waveform is constructed 304, the waveform is continuously displayed 306 therefore allowing the technician to view the entire, continuous blood pressure waveform.

The existing applanation state 308 is periodically determined and an error signal is computed 310 as a function of the difference between the actual applanation state 308 and the optimum applanation state 300. This error signal is applied to the control mechanism 312 for moving the tissue stress sensor in a way which minimizes, or eliminates, the error. From time to time, the optimum applanation state is redefined 316.

Mode 2: Applanation Fixed in Neighborhood of Optimum Applanation State

Figure 18A:
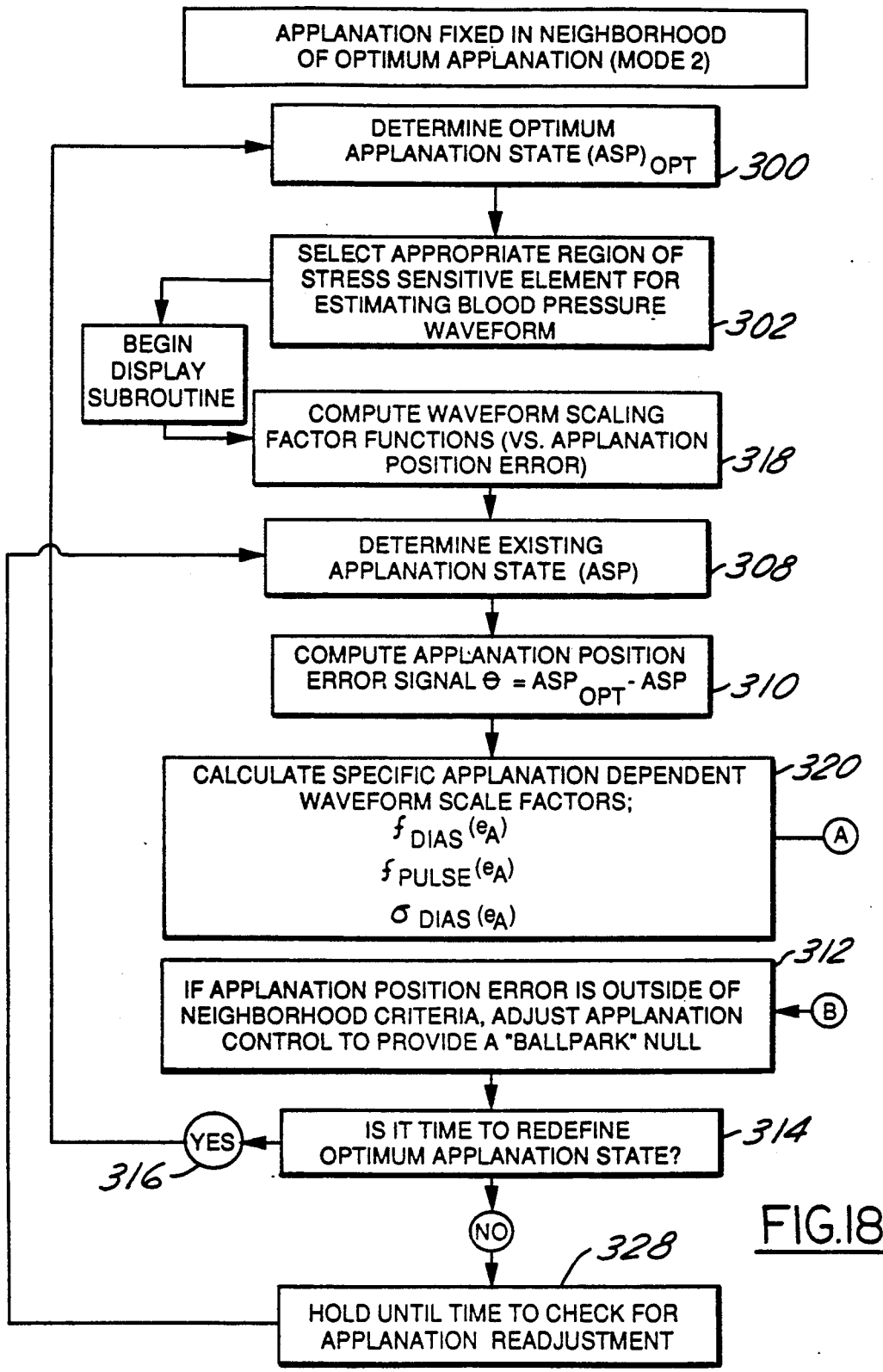
FIGS. 18A and 18B are logic flow diagrams showing a second mode of operation for continuously monitoring intra-arterial blood pressure.
Figure 18B:
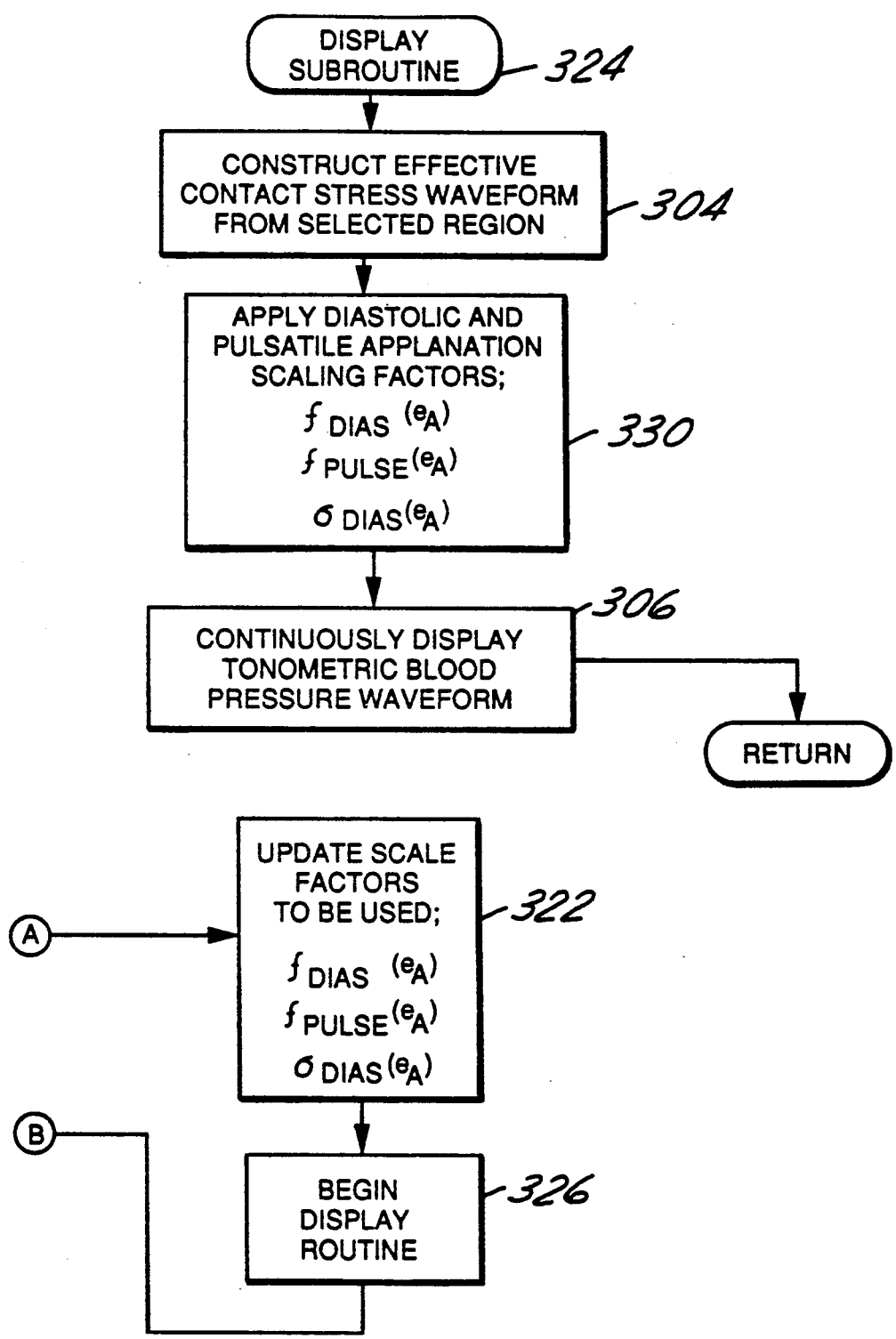

Now referring to FIGS. 18A and 18B, function blocks 300 through 316 operate identically to the similarly numbered function blocks set out in FIG. 17. Since blocks 300 through 316 have already been discussed in detail in conjunction with FIG. 17, a similar discussion will not be duplicated here.

Compute Waveform Scaling Factor Functions Versus Applanation Position Error

Unlike Mode 1, Mode 2 operates using the tissue stress sensor in an off-optimum (or non-optimum) applanation state. In order to use the tissue stress sensor in this way and still provide an accurate measure of intra-arterial blood pressure, scaling factors must be computed as a function of applanation position error 318. These scaling factors are then used to correct for the errors in the data generated by the tissue stress sensor. The method for computing these scaling factors as a function of applanation position error is set out below:

1. Using the data collected in function block 300, (which is the actual diastolic $(\sigma_{DIAS}(x,j))_{ACT}$ and pulse $(\sigma_{PULSE}(x,j))_{ACT}$ contact stress data collected as a function of distance along the stress sensitive element, x, and as a function of applanation state, j,), and 2. Using the region (a,b) computed in function block 302, 3. For each applanation state, j, construct the calculated effective diastolic $(\sigma_{DIAS}(j))_{EFF}$ and pulse $(\sigma_{PULSE}(j))_{EFF}$ contact stress values, where:

$$(\sigma_{DIAS}(j))_{EFF} = \frac{1}{b-a} \int_a^b (\sigma_{DIAS}(x,j))_{ACT} \cdot dx$$

$$(\sigma_{PULSE}(j))_{EFF} = \frac{1}{b-a} \int_a^b (\sigma_{PULSE}(x,j))_{ACT} \cdot dx$$

where:
a,b = define the boundaries of the region selected in function block 302.

4. Select an applanation state parameter ASP (see portion of specification entitled Defining and Utilizing Applanation Optimization Parameters and Applanation State Parameters set out earlier) and compute the ASP as a function of applanation state, j, (i.e. ASP(j)).

5. Combine the functions set out in steps 3 and 4 thereby relating the effective diastolic and pulse contact stress functions to ASP as follows:
$\sigma_{DIAS}(j)_{EFF}$ vs ASP(j); which yields $\sigma_{DIAS}(ASP)_{EFF}$
$\sigma_{PULSE}(j)_{EFF}$ vs ASP(j); which yields $\sigma_{PULSE}(ASP)_{EFF}$ 6. Having established the optimum applanation state $(ASP)_{OPT}$ (as set out in function block 300), use the functions set out in step 5 to define the effective diastolic and pulse contact stresses associated with the optimum applanation state $(ASP)_{OPT}$ (i.e.,$[\sigma_{DIAS}(ASP)_{EFF}]_{OPT}$, $[\sigma_{PULSE}(ASP)_{EFF}]_{OPT}$)

7. Using the function set out in step 4, generate applanation state error function, e, where:

$$e(ASP) = (ASP)_{OPT} - (ASP(j))$$

8. Using the functions set out in step 5, generate waveform scaling factor functions $f_{DIAS}$ and $f_{PULSE}$ as follows:

$$f_{DIAS}(ASP) = \frac{[\sigma_{DIAS}(ASP)_{EFF}]_{OPT}}{\sigma_{DIAS}(ASP)_{EFF}}$$

$$f_{PULSE}(ASP) = \frac{[\sigma_{PULSE}(ASP)_{EFF}]_{OPT}}{\sigma_{PULSE}(ASP)_{EFF}}$$

Figure 19:
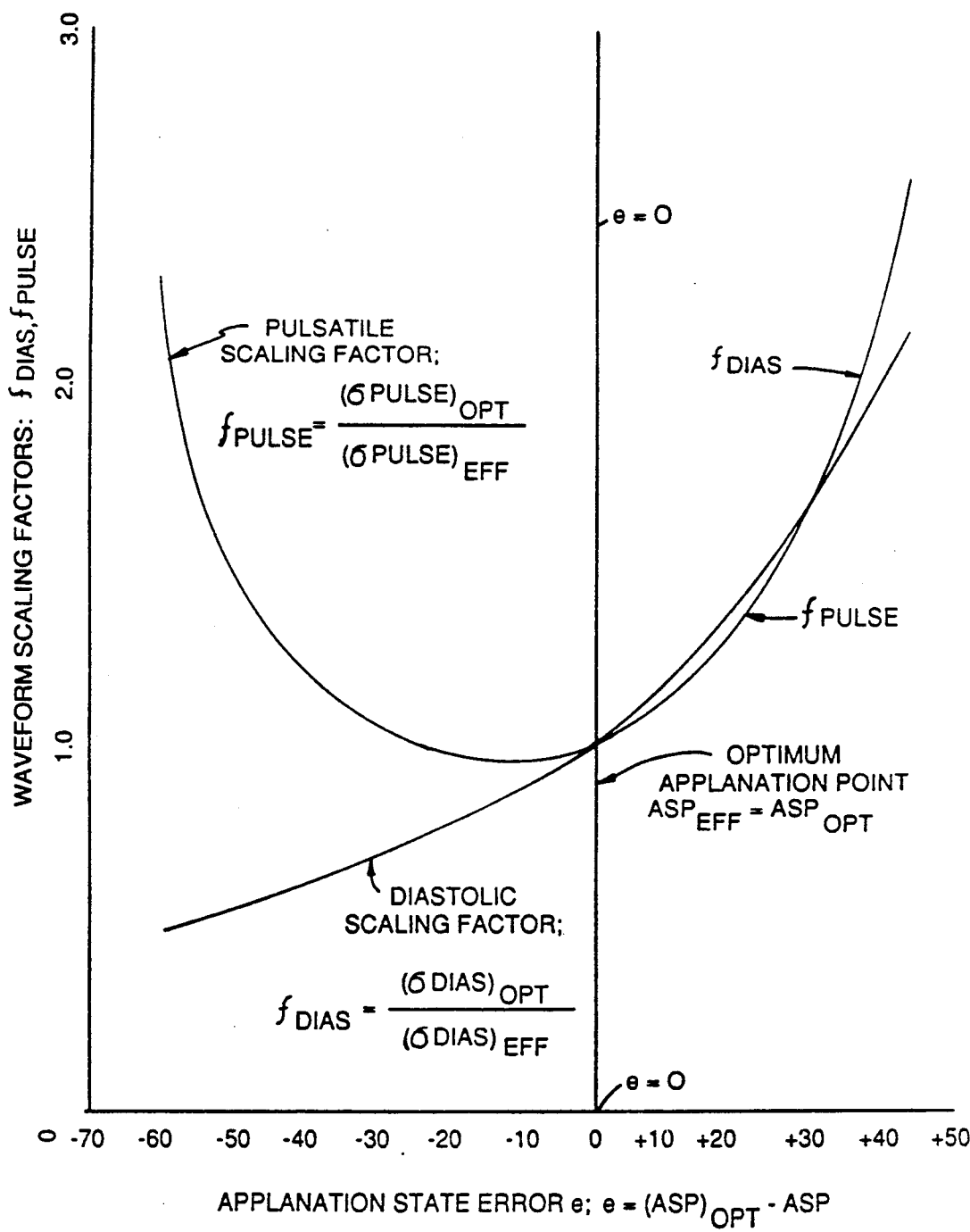
FIG. 19 is a graphical representation showing a method for calculating waveform scaling factors as a function of applanation state error.
Figure 20A:
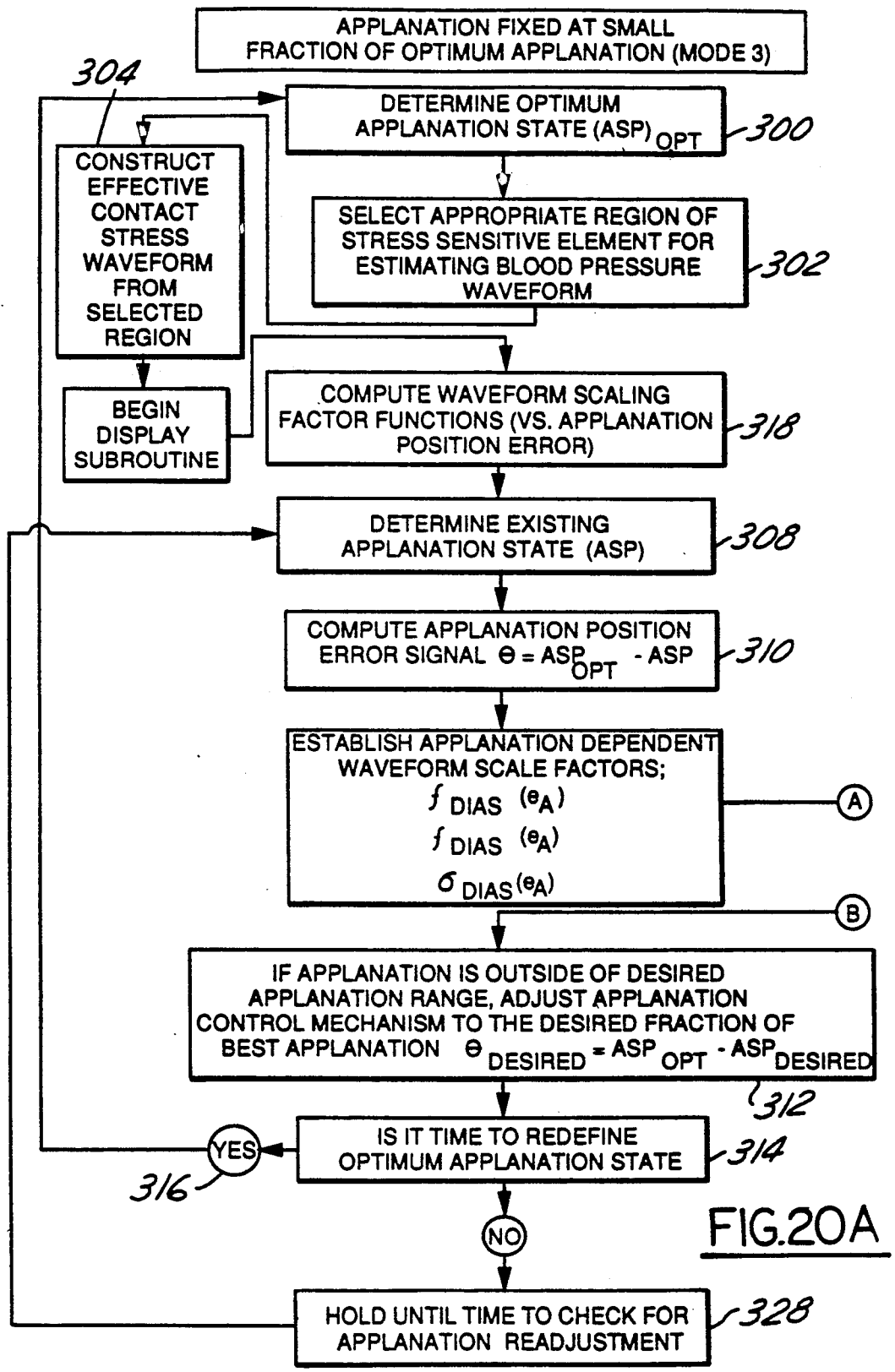
FIGS. 20A and 20B are logic flow diagrams showing a third mode of operation for continuously monitoring intra-arterial blood pressure.
Figure 20B:
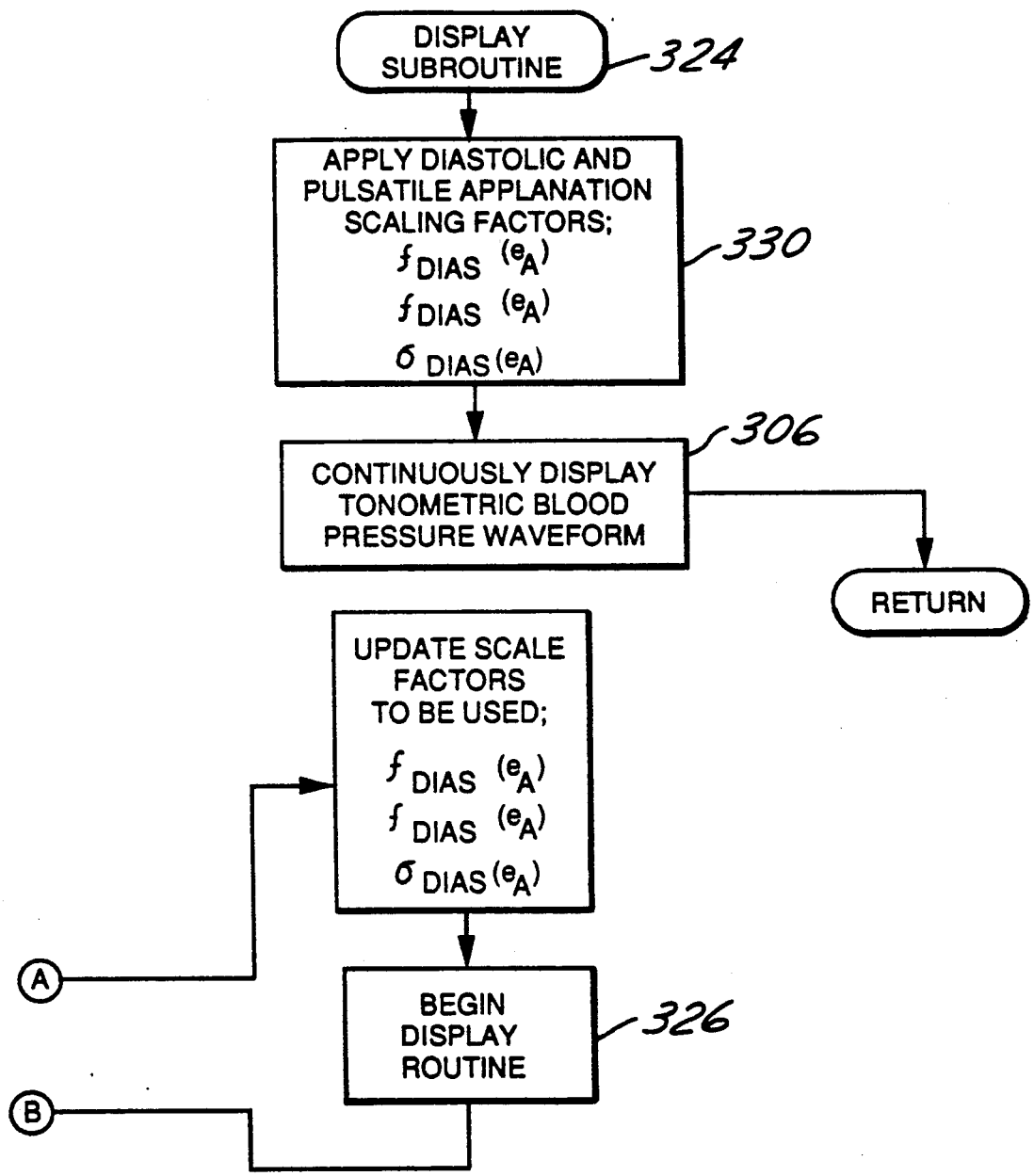

9. Combine the functions set out in steps 7 and 8 thereby relating the waveform scaling factor functions to the applanation error function as follows:
$f_{DIAS}(ASP)$ vs e(ASP); which yields $f_{DIAS}(e)$
$f_{PULSE}(ASP)$ vs e(ASP); which yields $f_{PULSE}(e)$
See FIG. 19 for a graphical representation of the $f_{DIAS}(e)$ and $f_{PULSE}(e)$ functions.

After the waveform scaling factor functions are computed 318, the existing applanation state is computed 308 in accordance with the procedures already set out for FIG. 17. Next, applanation position control error is calculated 310 as the difference between the optimum applanation state as determined in 300 and the actual applanation state as determined in 308. Based on the result of the error calculation 310, specific values ($f_{DIAS}(e_A)$, $f_{PULSE}(e_A)$, $\sigma_{DIAS}(e_A)$) are computed for the applanation dependent waveform scale factors by first calculating the error between optimum applanation $ASP_{OPT}$ and the existing or actual applanation ASP (i.e. $=ASP_{OPT}-ASP$) and then, finding the corresponding $f_{DIAS}$ and $f_{PULSE}$ values based on the relationship shown in FIG. 19. $\sigma_{DIAS}(e_A)$ is computed by dividing $(\sigma_{DIAS})_{OPT}$ by $f_{DIAS}(e_A)$. These three scale factors:

$f_{DIAS}(e_A)$
$f_{PULSE}(e_A)$
$\sigma_{DIAS}(e_A)$ are updated periodically or whenever a change in existing applanation state or a change in the optimum applanation state occurs.

Next, the three scale factors are updated 322 and made available to display routine 324.

Display routine 324 is called 326 and the tonometric blood pressure waveform is constructed and displayed. If the applanation position error is outside of predetermined limits, an adjustment is made to bring the tissue stress sensor within the predefined limits 312. Periodically 314, the tissue stress sensor is cycled through the complete range of movement to redefine the optimum applanation state. This redefinition can be performed based on any number of factors, including the duration of time the unit has been placed on the patient's arm, etc. If it is not time to redefine the optimum applanation state, the tissue stress sensor is held 328 until it is time to check for applanation position error 308.

Display routine 324 is responsible for constructing the effective contact stress waveform which is ultimately displayed to the operator. This process is similar to that which has already been disclosed in conjunction with FIG. 17 however, because we are no longer operating at the optimum applanation point, scaling factors must be applied to correct the contact stress waveform derived at the off-optimum applanation site 330. In order to estimate the true intra-arterial blood pressure waveform $[\sigma(t)]_{E.O.}$, the diastolic and pulse scaling factors are applied to the following formula.

$$[\sigma(t)]_{E.O.} = ([\sigma(t)]_A - \sigma_{DIAS}(e_A)) \cdot f_{PULSE}(e_A) + \sigma_{DIAS}(e_A) \cdot f_{DIAS}(e_A)$$

where:

$[\sigma(t)]_A$ = effective contact stress waveform from selected region acquired at known off-optimum applanation $f_{DIAS}(e_A)$ Scaling factors for
$f_{PULSE}(e_A)$ = known off-optimum
$\sigma_{DIAS}(e_A)$ applanation After the estimated effective contact stress waveform is constructed, it is displayed as a waveform which is continuous in time. The medium in which the waveform is displayed can be a strip chart recorder, cathode ray tube, LCD display, or any other convenient, suitable medium.

Mode 3: Applanation Fixed at a Small Fraction of Optimum Applanation State

The last mode of operation is completely analogous to the second mode of operation except that the error established in 312 will be, by design, much greater than the "ball park" error established in Mode 2. Thus by operating the stress sensitive element in this manner, patient comfort is increased.

The foregoing detailed description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. For example, although most of the methods disclosed herein deal primarily with continuous functions, all of the disclosed methods apply equally as well to methods utilizing discrete samples and discrete sample sets. Accordingly, it is to be understood that the subject matter sought to be afforded protection hereby should be deemed to extend to the subject matter defined in the appended claims, including all fair equivalents thereof.

We claim:

1. For use in a non-invasive blood pressure monitoring system, a method of operating a tissue stress sensor at an off-optimum arterial applanation state, said tissue stress sensor of the type for measuring the stress of tissue overlying an artery of interest, said method including the steps of:
   (A) placing said stress sensor in communication with said tissue overlying said artery of interest, and collecting stress datum from said sensor,
   (B) determining which of said datum corresponds to an optimum artery applanation state,
   (C) using said stress sensor for applanating said artery at said off-optimum applanation state,
   (D) obtaining from said tissue stress sensor stress datum associated with said tissue overlying said artery while said artery is in said off-optimum applanation state,
   (E) using said datum obtained in step (B) and step (D) and deriving correction factors, and
   (F) combining said stress data obtained in step (D) with said correction factors derived in step (E) to yield corrected stress data that approximates the intra-arterial blood pressure.

2. The method of claim 1, wherein step (B) includes the substeps of:
   (i) computing an applanation optimization factor (AOP) and an applanation state parameter (ASP),
   (ii) relating said AOP as a function of said ASP, and
   (iii) optimizing the relationship of substep (ii) according to a predetermined optimization rule.

3. The method of claim 2, wherein said AOP of substep (i) is a pulsatile stress parameter (PPAR) which is calculated according to the following formula:

$$PPAR = \frac{1}{c-b} \int_b^c (\sigma_{SCS}(x) - \sigma_{DCS}(x)) \cdot dx$$

where:
  b, c = limits of integration;
  $\sigma_{SCS}$ = systolic contact stress;
  $\sigma_{DCS}$ = diastolic contact stress;
  x = distance along stress sensitive element.

4. The method of claim 3, wherein the limits of integration b, c bound a continuous region of said stress sensor.

5. The method of claim 3, wherein said limits of integration b, c bound at least two discontinuous regions of said stress sensor.

6. The method of claim 2, wherein said ASP of substep (i) is an average contact stress parameter (AASI) which is calculated according to the following formula:

$$AASI_1 = \sigma_{AVG(AAS1)} = \frac{\int_0^L \sigma(x)_{AAS1}}{\int_0^L dx}$$

where:

$\sigma_{AVG}(AAS_1)$ = average stress value across the length of the stress sensitive element while the artery of interest undergoes the first artery applanation state;
$AAS_1$ = First Artery Applanation State;
$AASI_1$ = First Artery Applanation State Index;
$\sigma(x)_{AAS1}$ = stress data sensed by stress sensing element at location x while the artery of interest undergoes the first artery applanation state.

7. The method of claim 1, wherein step (F) includes combining stress data with said correction factors according to the following formula:

$$\sigma_{EFF}(t) = \sigma_{S.P.}(t) \cdot m + b$$

where:

$\sigma_{EFF}(t)$ = spatially corrected effective contact stress;
$\sigma_{S.P.}(t)$ = stress data obtained in step (C);
m = slope correction factor;
b = offset correction factor.

8. The method of claim 7, wherein said slope correction factor m and said offset correction factor b are derived according to the following formulas:

$$m = \frac{(\sigma^*_{DIAS})_{EFF} - (\sigma^*_{PULSE})_{EFF}}{(\sigma^*_{DIAS})_{S.P.} - (\sigma^*_{PULSE})_{S.P.}}$$

$$b = ((\sigma^*_{PULSE})_{EFF} - (\sigma^*_{PULSE})_{S.P.}) \cdot m$$

where:

$(\sigma^*_{DIAS})_{EFF}$ = effective diastolic contact stress associated with selected regions of the stress sensitive element;
$(\sigma^*_{PULSE})_{EFF}$ = effective pulsatile contact stress associated with selected regions of the stress sensitive element;
$(\sigma^*_{DIAS})_{S.P.}$ = diastolic contact stress associated with a specific sampling point along the stress sensitive element;
$(\sigma^*_{PULSE})_{S.P.}$ = pulsatile contact stress associated with a specific sampling point along the stress sensitive element.

9. The method of claim 8, wherein $(o^*_{DIAS})_{EFF}$ and $(o^*_{PULSE})_{EFF}$ are calculated according to the following formulas:

$$(\sigma^*_{DIAS})_{EFF} = \frac{1}{b-c} \int_b^c \sigma^*_{DIAS}(x) \cdot dx$$

$$= \frac{1}{N} \sum_{i=1}^{N} (\sigma^*_{DIAS})_i$$

$$(\sigma^*_{PULSE})_{EFF} = \frac{1}{b-c} \int_b^c \sigma^*_{PULSE}(x) \cdot dx$$

$$= \frac{1}{N} \sum_{i=1}^{N} (\sigma^*_{PULSE}(i))$$

where:

$o^*_{DIAS}(x)$ = diastolic contact stress;
$o^*_{PULSE}(x)$ = pulsatile contact stress;
x = location along stress sensitive element;
b, c = limits of integration;
i = discrete location along stress sensitive element.

10. The method of claim 1, wherein step (F) includes combining said stress data with said correction factors according to the following formula:

$$(\sigma(t))_{E.O.} = ((\sigma(t))_A - \sigma_{DIAS(eA)}) \cdot f_{PULSE(eA)} + \sigma_{DIAS(eA)} \cdot f_{DIAS(eA)}$$

where:

$(o(t))_A$ = effective contact stress waveform from selected region acquired at known off-optimum applanation;

$f_{DIAS(eA)}$     Scaling factors for
$f_{PULSE(eA)}$ = known off-optimum
$\sigma_{DIAS(eA)}$     applanation.

11. The method of claim 10, wherein said scaling factors are derived according to the following formulas:

$$f_{DIAS(eA)} = \frac{(\sigma_{DIAS(ASP)EFF})_{OPT}}{\sigma_{DIAS(ASP)EFF}}$$

$$f_{PULSE(eA)} = \frac{(\sigma_{PULSE(ASP)EFF})_{OPT}}{\sigma_{PULSE(ASP)EFF}}$$

$$\sigma_{DIAS(eA)} = \frac{(\sigma_{DIAS})_{OPT}}{f_{DIAS(eA)}}$$

where:

$(o_{DIAS}(ASP)_{EFF})_{OPT}$ = effective diastolic contact stress at the optimum applanation state;
$o_{DIAS}(ASP)_{EFF}$ = effective diastolic contact stress at the actual off optimum applanation state;
$(o_{PULSE}(ASP)_{EFF})_{OPT}$ = effective pulsatile contact stress at the optimum applanation state;
$o_{PULSE}(ASP)_{EFF}$ = effective pulsatile contact stress at the actual off optimum applanation state;
$(o_{DIAS})_{OPT}$ = diastolic contact stress at optimum applanation state.

12. For use in a non-invasive blood pressure monitoring system, a method of operating a tissue stress sensor at a non-optimum arterial applanation state, said tissue stress sensor including a stress sensitive element for measuring the stress of tissue overlying an artery of interest, said stress sensitive element having a length that exceeds the diameter of the lumen of said artery of interest, said method including the steps of:

(A) placing said stress sensitive element of said tissue stress sensor in communication with said tissue overlying said artery of interest, (B) orienting said stress sensitive element such that said stress sensitive element spans beyond the diameter of the lumen of said artery of interest, (C) using said stress sensitive element to act upon said artery of interest thereby applanating said artery of interest through a plurality of applanation states, and at each applanation state, (D) obtaining from said tissue stress sensor at least one electrical signal representing stress data across the length of said stress sensitive element, each stress datum of said stress data representing stress datum communicated to a predetermined portion of said stress sensitive element from said tissue overlying said artery of interest, and from said data obtained in at least one of said plurality of applanation states, (E) determining an optimum arterial applanation state, (F) computing an error value associated with said non-optimum arterial applanation state wherein said non-optimum arterial applanation state is different from said optimum arterial applanation sate, (G) applanating said artery of interest to said non-optimum arterial applanation state, (H) while said artery is applanated to said non-optimum applanation state, obtaining tissue stress data from said tissue stress sensor, and (I) combining said stress data obtained in step (H) with said error value computed in step (F) to yield corrected stress data that approximates stress data associated with said tissue overlying said artery of interest when said artery is applanated to said optimum arterial applanation state.

13. The method of claim 12, wherein step (E) includes the substeps of:
(i) computing an applanation optimization factor (AOP) and an applanation state parameter (ASP),
(ii) relating said AOP as a function of said ASP, and
(iii) optimizing the relationship of substep (ii) according to a predetermined optimization rule.

14. The method of claim 13, wherein said AOP of substep (i) is a pulsatile stress parameter (PPAR) which is calculated according to the following formula:

$$PPAR = \frac{1}{c-b} \int_b^c (\sigma_{SCS}(x) - \sigma_{DCS}(x)) \cdot dx$$

where:
b, c = limits of integration;
$\sigma_{SCS}$ = systolic contact stress;
$\sigma_{DCS}$ = diastolic contact stress;
x = distance along stress sensitive element.

15. The method of claim 14, wherein the limits of integration b,c bound a continuous region of said stress sensor.

16. The method of claim 14, wherein said limits of integration b,c bound at least two discontinuous regions of said stress sensor.

17. The method of claim 13, wherein said ASP of substep (i) is an average contact stress parameter (AASI) which is calculated according to the following formula:

$$AASI_1 = \sigma_{AVG(AAS1)} = \frac{\int_0^L \sigma(x)_{AAS1}}{\int_0^L dx}$$

where:
$\sigma_{AVG(AAS1)}$ = average stress value across the length of the stress sensitive element while the artery of interest undergoes the first artery applanation state;
$AAS_1$ = First Artery Applanation State;
$AASI_1$ = First Artery Applanation State Index;
$\sigma(x)_{AAS1}$ = stress data sensed by stress sensing element at location x while the artery of interest undergoes the first artery applanation state.

18. The method of claim 12, wherein step (I) includes combining stress data with said error value according to the following formula:

$$\sigma_{EFF}(t) = \sigma_{S.P.}(t) \cdot m + b$$

where:
$\sigma_{EFF}(t)$ = spatially corrected effective contact stress;
$\sigma_{S.P.}(t)$ = stress data obtained in step (C);
m = slope correction factor;
b = offset correction factor.

19. The method of claim 18, wherein said slope correction factor m and said offset correction factor b are derived according to the following formulas:

$$m = \frac{(\sigma^*_{DIAS})_{EFF} - (\sigma^*_{PULSE})_{EFF}}{(\sigma^*_{DIAS})_{S.P.} - (\sigma^*_{PULSE})_{S.P.}}$$

$$b = ((\sigma^*_{PULSE})_{EFF} - (\sigma^*_{PULSE})_{S.P.}) \cdot m$$

where:
$(\sigma^*_{DIAS})_{EFF}$ = effective diastolic contact stress associated with selected regions of the stress sensitive element;
$(\sigma^*_{PULSE})_{EFF}$ = effective pulsatile contact stress associated with selected regions of the stress sensitive element;
$(\sigma^*_{DIAS})_{S.P.}$ = diastolic contact stress associated with a specific sampling point along the stress sensitive element;
$(\sigma^*_{PULSE})_{S.P.}$ = pulsatile contact stress associated with a specific sampling point along the stress sensitive element.

20. The method of claim 12, wherein step (I) includes combining said stress data with said error value according to the following formula:

$$(\sigma(t))_{E.O.} = ((\sigma(t))_A - \sigma_{DIAS}(e_A)) \cdot f_{PULSE}(e_A) + \sigma_{DIAS}(e_A) \cdot f_{DIAS}(e_A)$$

where:
$(\sigma(t))_A$ = effective contact stress waveform from selected region acquired at known off-optimum applanation;

$f_{DIAS}(e_A)$ Scaling factors for
$f_{PULSE}(e_A)$ = known off-optimum
$\sigma_{DIAS}(e_A)$ applanation.

21. The method of claim 20, wherein said scaling factors are derived according to the following formulas:

$$f_{DIAS}(e_A) = \frac{(\sigma_{DIAS}(ASP)_{EFF})_{OPT}}{\sigma_{DIAS}(ASP)_{EFF}}$$

$$f_{PULSE}(e_A) = \frac{(\sigma_{PULSE}(ASP)_{EFF})_{OPT}}{\sigma_{PULSE}(ASP)_{EFF}}$$

$$\sigma_{DIAS}(e_A) = \frac{(\sigma_{DIAS})_{OPT}}{f_{DIAS}(e_A)}$$

where:
- $(\sigma_{DIAS}(ASP)_{EFF})_{OPT}$ = effective diastolic contact stress at the optimum applanation state;
- $\sigma_{DIAS}(ASP)_{EFF}$ = effective diastolic contact stress at the actual off-optimum applanation state;
- $(\sigma_{PULSE}(ASP)_{EFF})_{OPT}$ = effective pulsatile contact stress at the optimum applanation state;
- $\sigma_{PULSE}(ASP)_{EFF}$ = effective pulsatile contact stress at the actual off-optimum applanation state;
- $(\sigma_{DIAS})_{OPT}$ = diastolic contact stress at optimum applanation state.

22. For use in a non-invasive blood pressure monitoring system, an apparatus for operating a tissue stress sensor at an off-optimum arterial applanation state, said tissue stress sensor of the type for measuring the stress of tissue overlying an artery of interest, said apparatus comprising:
- means for placing said stress sensor in communication with said tissue overlying said artery of interest, and means for collecting stress datum from said sensor,
- means for determining which of said datum corresponds to an optimum artery applanation state,
- means for applanating said artery at said off-optimum applanation state,
- means for obtaining from said tissue stress sensor stress datum associated with said tissue overlying said artery while said artery is in said off-optimum applanation state,
- means for deriving correction factors using said datum corresponding to said optimum applanation state and said off-optimum applanation state, and
- means for combining said stress data corresponding to said off-optimum applanation state with said correction factors to yield corrected stress data that approximates the intra-arterial blood pressure.

23. The apparatus of claim 22, wherein said combining means combines stress data with said correction factors according to the following formula:

$$\sigma_{EFF}(t) = \sigma_{S.P.}(t) \cdot m + b$$

where:
- $\sigma_{EFF}(t)$ = spatially corrected effective contact stress;
- $\sigma_{S.P.}(t)$ = stress data obtained in step (C);
- m = slope correction factor;
- b = offset correction factor.

24. The apparatus of claim 22, wherein said combining means combines said stress data with said correction factors according to the following formula:

$$(\sigma(t))_{E.O.} = ((\sigma(t))_A - \sigma_{DIAS}(e_A)) \cdot f_{PULSE}(e_A) + \sigma_{DIAS}(e_A) \cdot f_{DIAS}(e_A)$$

where:
- $(\sigma(t))_A$ = effective contact stress waveform from selected region acquired at known off-optimum applanation;

$f_{DIAS}(e_A)$
$f_{PULSE}(e_A)$ = Scaling factors for known off-optimum applanation.
$\sigma_{DIAS}(e_A)$ 25. The apparatus of claim 24, wherein said combining means uses scaling factors derived according to the following formula:

$$f_{DIAS}(e_A) = \frac{(\sigma_{DIAS}(ASP)_{EFF})_{OPT}}{\sigma_{DIAS}(ASP)_{EFF}}$$

$$f_{PULSE}(e_A) = \frac{(\sigma_{PULSE}(ASP)_{EFF})_{OPT}}{\sigma_{PULSE}(ASP)_{EFF}}$$

$$\sigma_{DIAS}(e_A) = \frac{(\sigma_{DIAS})_{OPT}}{f_{DIAS}(e_A)}$$

where:
- $(\sigma_{DIAS}(ASP)_{EFF})_{OPT}$ = effective diastolic contact stress at the optimum applanation state;
- $\sigma_{DIAS}(ASP)_{EFF}$ = effective diastolic contact stress at the actual off optimum applanation state;
- $(\sigma_{PULSE}(ASP)_{EFF})_{OPT}$ = effective pulsatile contact stress at the optimum applanation state;
- $\sigma_{PULSE}(ASP)_{EFF}$ = effective pulsatile contact stress at the actual off optimum applanation state;
- $(\sigma_{DIAS})_{OPT}$ = diastolic contact stress at optimum applanation state.

* * * * *

UNITED STATES PATENT AND TRADEMARK OFFICE
CERTIFICATE OF CORRECTION

PATENT NO.   :   5,261,412

DATED        :   November 16, 1993

INVENTOR(S)  :   Butterfield, et al.

It is certified that error appears in the above-identified patent and that said Letters Patent is hereby corrected as shown below:

Col. 25, line 26, "sate" should read --state--.

Signed and Sealed this

Seventeenth Day of May, 1994

Attest:

BRUCE LEHMAN

Attesting Officer

Commissioner of Patents and Trademarks